US011291431B2

(12) United States Patent
Komatsu et al.

(10) Patent No.: US 11,291,431 B2
(45) Date of Patent: Apr. 5, 2022

(54) EXAMINATION ASSISTING METHOD, EXAMINATION ASSISTING APPARATUS, AND COMPUTER-READABLE RECORDING MEDIUM

(71) Applicants: FUJITSU LIMITED, Kawasaki (JP); RIKEN, Wako (JP); SHOWA UNIVERSITY, Tokyo (JP); NATIONAL CANCER CENTER, Tokyo (JP)

(72) Inventors: Masaaki Komatsu, Koto (JP); Hiroyuki Yoshida, Machida (JP); Akira Sakai, Kawasaki (JP); Akihiko Sekizawa, Shinagawa (JP); Ryu Matsuoka, Shinagawa (JP); Ryuji Hamamoto, Chuo (JP)

(73) Assignees: FUJITSU LIMITED, Kawasaki (JP); RIKEN, Wako (JP); SHOWA UNIVERSITY, Tokyo (JP); NATIONAL CANCER CENTER, Tokyo (JP)

( * ) Notice: Subject to any disclaimer, the term of this patent is extended or adjusted under 35 U.S.C. 154(b) by 5 days.

(21) Appl. No.: 16/544,924

(22) Filed: Aug. 20, 2019

(65) Prior Publication Data

US 2020/0060659 A1 Feb. 27, 2020

(30) Foreign Application Priority Data

Aug. 24, 2018 (JP) ............................ JP2018-157844

(51) Int. Cl.
*A61B 8/00* (2006.01)
*A61B 8/08* (2006.01)
(Continued)

(52) U.S. Cl.
CPC ........... *A61B 8/5269* (2013.01); *A61B 8/463* (2013.01); *G06T 7/0016* (2013.01); *G06T 7/11* (2017.01);
(Continued)

(58) Field of Classification Search
None
See application file for complete search history.

(56) References Cited

U.S. PATENT DOCUMENTS 3,570,279 A * 3/1971 Davies .................. G01B 17/02 73/615
7,556,602 B2 * 7/2009 Wang .................... A61B 6/463 600/437
(Continued)

OTHER PUBLICATIONS

Salehi et al., "Precise Ultrasound Bone Registration with Learning-Based Segmentation and Speed of Sound Calibration," Medical Image Computing and Computer-Assisted Intervention—MICCAI 2017. Lecture Notes in Computer Science, vol. 10434. Springer, Cham (Year: 2017).*
(Continued)

*Primary Examiner* — Soo Shin
(74) *Attorney, Agent, or Firm* — Xsensus LLP

(57) ABSTRACT

A non-transitory computer-readable recording medium stores therein an examination assisting program that causes a computer to execute a process including: performing a site detecting process that uses an object detection technique on each of a plurality of ultrasound examination images taken of an examined subject by performing a scan on the examined subject; and displaying a site detection map in which a detection result of each of a plurality of sites included in the examined subject is kept in correspondence with the scan, on a basis of detection results from the site detecting process.

13 Claims, 20 Drawing Sheets

11

OBJECT DETECTION TECHNIQUE

12

13

| CROSS-SECTIONAL PLANE | 1 | 2 | 3 | 4 | 5 | 6 | 7 | 8 | 9 |
|---|---|---|---|---|---|---|---|---|---|
| SITE A | U | U | U | S | S | U | S | U | U |
| SITE B | U | U | U | I | S | U | S | U | U |
| SITE C | S | S | I | U | U | U | U | U | U |
| SITE D | S | S | I | U | U | U | U | U | U |
| SITE E | U | U | U | I | S | S | U | U | U |
| SITE F | U | U | U | S | S | S | S | U | U |

S: DETECTED WITH SUFFICIENT PROBABILITY
I: DETECTED WITH INSUFFICIENT PROBABILITY
U: UNDETECTED

(51) Int. Cl.

| | |
|---|---|
| ***G06T 7/00*** | (2017.01) |
| ***G06T 7/11*** | (2017.01) |
| ***G06T 7/143*** | (2017.01) |
| ***G06T 7/174*** | (2017.01) |
| ***G16H 50/30*** | (2018.01) |

(52) U.S. Cl.

CPC .............. *G06T 7/143* (2017.01); *G06T 7/174* (2017.01); *G06T 2207/10132* (2013.01)

(56) References Cited

U.S. PATENT DOCUMENTS

| | | | | |
|---|---|---|---|---|
| 10,910,097 | B2 * | 2/2021 | Bernard | G06K 9/6215 |
| 2009/0088981 | A1 * | 4/2009 | Neville | G16H 50/20 702/19 |
| 2010/0063393 | A1 * | 3/2010 | Moradi | A61B 8/0833 600/442 |
| 2013/0266197 | A1 * | 10/2013 | Nagenthiraja | G06T 7/149 382/128 |
| 2013/0310680 | A1 * | 11/2013 | Werahera | A61B 8/461 600/411 |
| 2019/0206565 | A1 * | 7/2019 | Shelton, IV | A61B 34/74 |
| 2020/0060659 | A1 * | 2/2020 | Komatsu | A61B 8/4245 |

OTHER PUBLICATIONS

Wee et al., "Automatic Detection of Fetal Nasal Bone in 2 Dimensional Ultrasound Image Using Map Matching," Proceedings of the 12th WSEAS International Conference on Automatic Control, Modelling & Simulation, May 2010, pp. 305-309 (Year: 2010).*

Dudley et al., "Blinded Comparison between an In-Air Reverberation Method and an Electronic Probe Tester in the Detection of Ultrasound Probe Faults," Ultrasound in Medicine & Biology, vol. 43, Issue 12, Dec. 2017, pp. 2954-2958 (Year: 2017).*

Sadeghi et al., "30Hz Object Detection with DPM V5", In Computer Vision—ECCV 2014, Sep. 6-12, 2014, pp. 65-79.

Redmon et al., "You Only Look Once: Unified, Real-Time Object Detection", arXiv:1506.02640v5 [cs.CV], May 9, 2016, 10 pages.

* cited by examiner

| CROSS-SECTIONAL PLANE | 1 | 2 | 3 | 4 | 5 | 6 | 7 | 8 | 9 |
|---|---|---|---|---|---|---|---|---|---|
| SITE A | U | U | U | S | S | U | S | U | U |
| SITE B | U | U | U | I | S | U | S | U | U |
| SITE C | S | S | I | U | U | U | U | U | U |
| SITE D | S | S | I | U | U | U | U | U | U |
| SITE E | U | U | U | I | S | S | U | U | U |
| SITE F | U | U | U | S | S | S | S | U | U |

| CROSS-SECTIONAL PLANE | 1 | 2 | 3 | 4 | 5 | 6 | 7 | 8 | 9 |
|---|---|---|---|---|---|---|---|---|---|
| SITE A | U | U | U | S | S | U | S | U | U |
| SITE B | U | U | U | S | S | U | S | U | U |
| SITE C | S | S | S | U | U | U | U | U | U |
| SITE D | S | S | S | U | U | U | U | U | U |
| SITE E | U | U | U | S | S | U | U | U | U |
| SITE F | U | U | U | S | S | U | S | U | U |

S: DETECTED WITH SUFFICIENT PROBABILITY
I: DETECTED WITH INSUFFICIENT PROBABILITY
U: UNDETECTED

| CROSS-SECTIONAL PLANE | 1 | 2 | 3 | 4 | 5 | 6 | 7 | 8 | 9 |
|---|---|---|---|---|---|---|---|---|---|
| SITE A | U | U | U | S | S | U | S | U | U |
| SITE B | U | U | U | U | U | U | U | U | U |
| SITE C | S | S | S | U | U | U | U | U | U |
| SITE D | S | S | S | U | U | U | U | U | U |
| SITE E | U | U | U | S | S | U | U | U | U |
| SITE F | U | U | U | S | S | U | S | U | U |

S: DETECTED WITH SUFFICIENT PROBABILITY
I: DETECTED WITH INSUFFICIENT PROBABILITY
U: UNDETECTED

| CROSS-SECTIONAL PLANE | 1 | 2 | 3 | 4 | 5 | 6 | 7 | 8 | 9 |
|---|---|---|---|---|---|---|---|---|---|
| SITE A | U | U | U | S | S | U | S | U | U |
| SITE B | U | U | U | I | I | U | I | U | U |
| SITE C | S | S | S | U | U | U | U | U | U |
| SITE D | S | S | S | U | U | U | U | U | U |
| SITE E | U | U | U | S | S | U | U | U | U |
| SITE F | U | U | U | S | S | U | S | U | U |

S: DETECTED WITH SUFFICIENT PROBABILITY
I: DETECTED WITH INSUFFICIENT PROBABILITY
U: UNDETECTED

| CROSS-SECTIONAL PLANE | 1 | 2 | 3 | 4 | 5 | 6 | 7 | 8 | 9 |
|---|---|---|---|---|---|---|---|---|---|
| SITE A | U | U | U | S | U | U | U | U | U |
| SITE B | U | U | U | S | U | U | U | U | U |
| SITE C | U | U | S | U | U | U | U | U | U |
| SITE D | U | U | S | U | U | U | U | U | U |
| SITE E | U | U | U | S | U | U | U | U | U |
| SITE F | U | U | U | S | U | U | U | U | U |

S: DETECTED WITH SUFFICIENT PROBABILITY
I: DETECTED WITH INSUFFICIENT PROBABILITY
U: UNDETECTED

| CROSS-SECTIONAL PLANE | 1 | 2 | 3 | 4 | 5 | 6 | 7 | 8 | 9 |
|---|---|---|---|---|---|---|---|---|---|
| SITE A | U | U | U | S | U | U | S | U | U |
| SITE B | U | U | U | S | U | U | S | U | U |
| SITE C | U | S | S | U | U | U | U | U | U |
| SITE D | U | S | S | U | U | U | U | U | U |
| SITE E | U | U | U | S | U | U | S | U | U |
| SITE F | U | U | U | S | U | U | S | U | U |

S: DETECTED WITH SUFFICIENT PROBABILITY
I: DETECTED WITH INSUFFICIENT PROBABILITY
U: UNDETECTED

: UNDETECTED

: DETECTED (WITH PROBABILITY LOWER THAN 20%)

: DETECTED (WITH PROBABILITY OF 20% OR HIGHER)

No. 212

No. 131

FIG.18
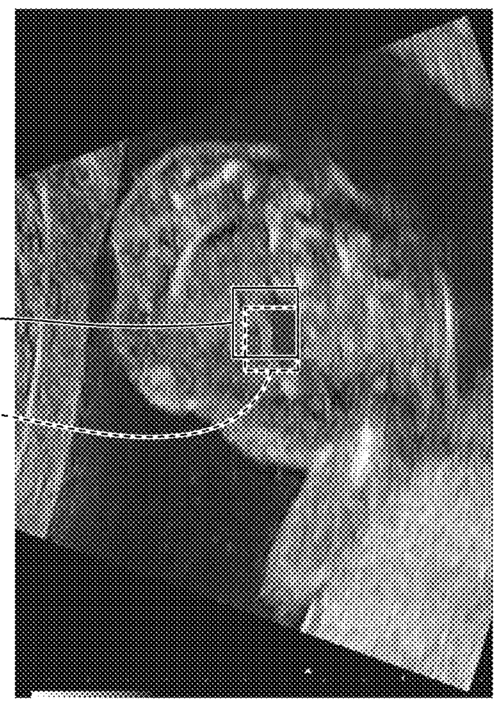
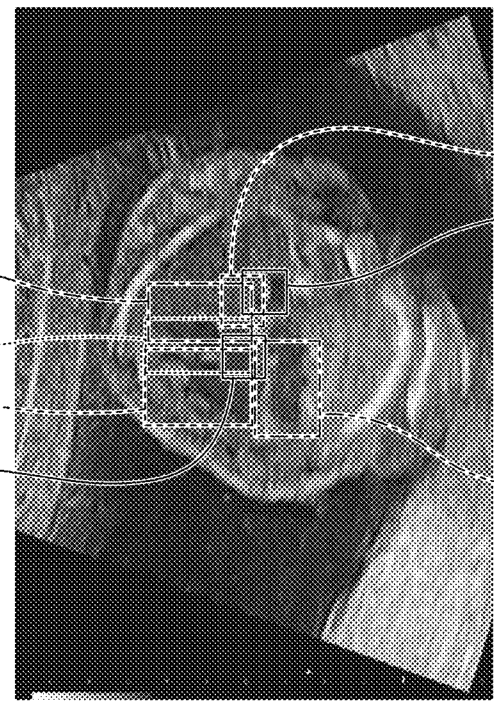

64
MOVE PROBE IN ONE DIRECTION
65
60
61
62
63
62
60

68

| CROSS-SECTIONAL PLANE | 1 | 2 | 3 | 4 | 5 | 6 | 7 | 8 | 9 |
|---|---|---|---|---|---|---|---|---|---|
| CHIP 62a | U | S | S | S | S | U | U | U | U |
| CHIP 62b | U | U | U | U | U | U | S | S | S |
| CHIP 62c | U | U | S | S | S | S | S | U | U |

S: DETECTED WITH SUFFICIENT PROBABILITY
I: DETECTED WITH INSUFFICIENT PROBABILITY
U: UNDETECTED

EXAMINATION ASSISTING METHOD, EXAMINATION ASSISTING APPARATUS, AND COMPUTER-READABLE RECORDING MEDIUM

CROSS-REFERENCE TO RELATED APPLICATION(S)

This application is based upon and claims the benefit of priority of the prior Japanese Patent Application No. 2018-157844, filed on Aug. 24, 2018, the entire contents of which are incorporated herein by reference.

FIELD

The embodiments discussed herein are related to an examination assisting method, an examination assisting apparatus, and a computer-readable recording medium.

BACKGROUND

Ultrasound examinations are known by which a subject is examined without being destructed as to whether the internal structure thereof has an abnormality or not. In an ultrasound examination, for example, a two-dimensionally scanned cross-sectional plane of an examined subject is imaged, so as to perform the examination by checking the image of the scanned cross-sectional plane. Because a probe used for the imaging process is operated by a person to perform the scan, for example, the image of the scanned cross-sectional plane is strongly affected by changes in the imaging environment. For this reason, in many situations, the image of the scanned cross-sectional plane, i.e., the ultrasound examination image is visually checked. Further, among techniques used for providing information useful for diagnosing processes, a technique is known by which a three-dimensional model is generated from a scan result obtained by implementing Computed Tomography (CT), Magnetic Resonance Imaging (MRI), or the like, so as to present information about an arbitrary cross-sectional plane.

Further, object detection techniques are also known by which it is detected what kind of object is rendered in an image. Among the object detection techniques, as methods for detecting an object in an image by machine learning, for example, Deformable Parts Model (DPM) schemes and You Only Look Once (YOLO) schemes have been proposed.

Non Patent Document 1: M. A. Sadeghi and D. Forsyth, "30 Hz Object Detection with DPM V5", In Computer Vision-ECCV 2014, pages 65-79, Springer, 2014 Non-Patent Document 2: Joseph Redmon, Santosh Divvala, Ross Girshick, Ali Farhadi, "You Only Look Once: Unified, Real-Time Object Detection", arXiv:1506.02640v5 [cs.CV], 9 May 2016

However, ultrasound examinations involve checking each of a plurality of sites from a plurality of images. Accordingly, there is a large burden of performing an operation to select the images in which statuses of the sites are to be checked. In other words, the ultrasound examinations impose a large burden of judging whether an abnormality is present or absent.

SUMMARY

According to an aspect of an embodiment, a non-transitory computer-readable recording medium stores therein an examination assisting program that causes a computer to execute a process including: performing a site detecting process that uses an object detection technique on each of a plurality of ultrasound examination images taken of an examined subject by performing a scan on the examined subject; and displaying a site detection map in which a detection result of each of a plurality of sites included in the examined subject is kept in correspondence with the scan, on a basis of detection results from the site detecting process.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 8 is a drawing illustrating an example of the site detection map exhibiting a normal pattern;

FIG. 10 is a drawing illustrating another example of the site detection map exhibiting an abnormal pattern;

FIG. 11 is a drawing illustrating an example of the site detection map exhibiting an undeterminable pattern;

FIG. 12 is a drawing illustrating another example of the site detection map exhibiting an undeterminable pattern;

FIG. 18 is a drawing illustrating other examples of the site detection results;

DESCRIPTION OF EMBODIMENTS

Preferred embodiments will be explained with reference to accompanying drawings. The present disclosure is not limited to the embodiments described below. Further, it is possible to combine together any of the embodiments described below, as long as no conflict occurs.

[a] First Embodiment

Figure 1:
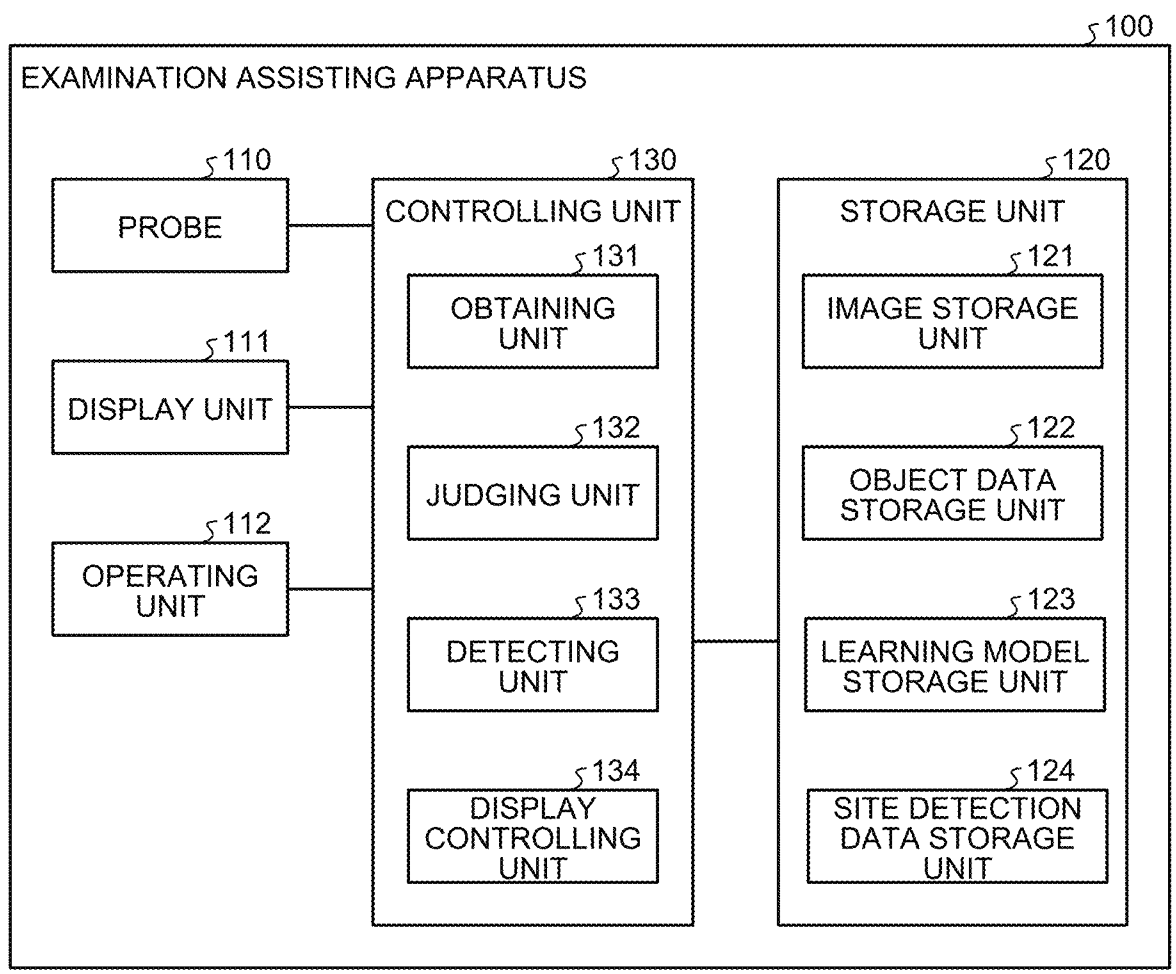
FIG. 1 is a block diagram illustrating an exemplary configuration of an examination assisting apparatus according to a first embodiment.

FIG. 1 is a block diagram illustrating an exemplary configuration of an examination assisting apparatus according to a first embodiment. An examination assisting apparatus 100 illustrated in FIG. 1 performs a site detecting process that uses an object detection technique on each of a plurality of ultrasound examination images taken of an examined subject by performing a scan thereon. On the basis of detection results from the site detecting process (hereinafter "detection results"), the examination assisting apparatus 100 displays a site detection map in which a detection result of each of the plurality of sites included in the examined subject is kept in correspondence with the scan. As a result, the examination assisting apparatus 100 is able to provide the site detection map that makes it possible to easily judge whether an abnormality is present or absent.

First, an object detecting process in the ultrasound examination according to the present embodiment will be explained. In situations where ultrasound examinations are performed, objects serving as examined subjects have a certain internal structure in many situations. For this reason, during the ultrasound examinations, it is possible to estimate a structure that is supposed to be present on the basis of information about positions of a probe or the like, by using knowledge from examinations, a design drawing, or the like. Accordingly, in the present embodiment, with respect to an examined subject of which the internal structure in a normal state is known, a site detection map indicating a detection result of each of the sites is generated by comparing an internal structure detected by using an object detection technique employing machine learning, with a normal structure that is supposed to be present. In the current situation, although the object detection technique using machine learning is not as good as the level of human beings (an average precision level mAP=approximately 80), it is possible to calculate sufficiently reliable results by applying a statistical process to processing results. Further, in the present embodiment, an example will be explained in which a fetal heart will be used as an examined subject. However, the present disclosure is also applicable to other organs and the like.

Figure 2:
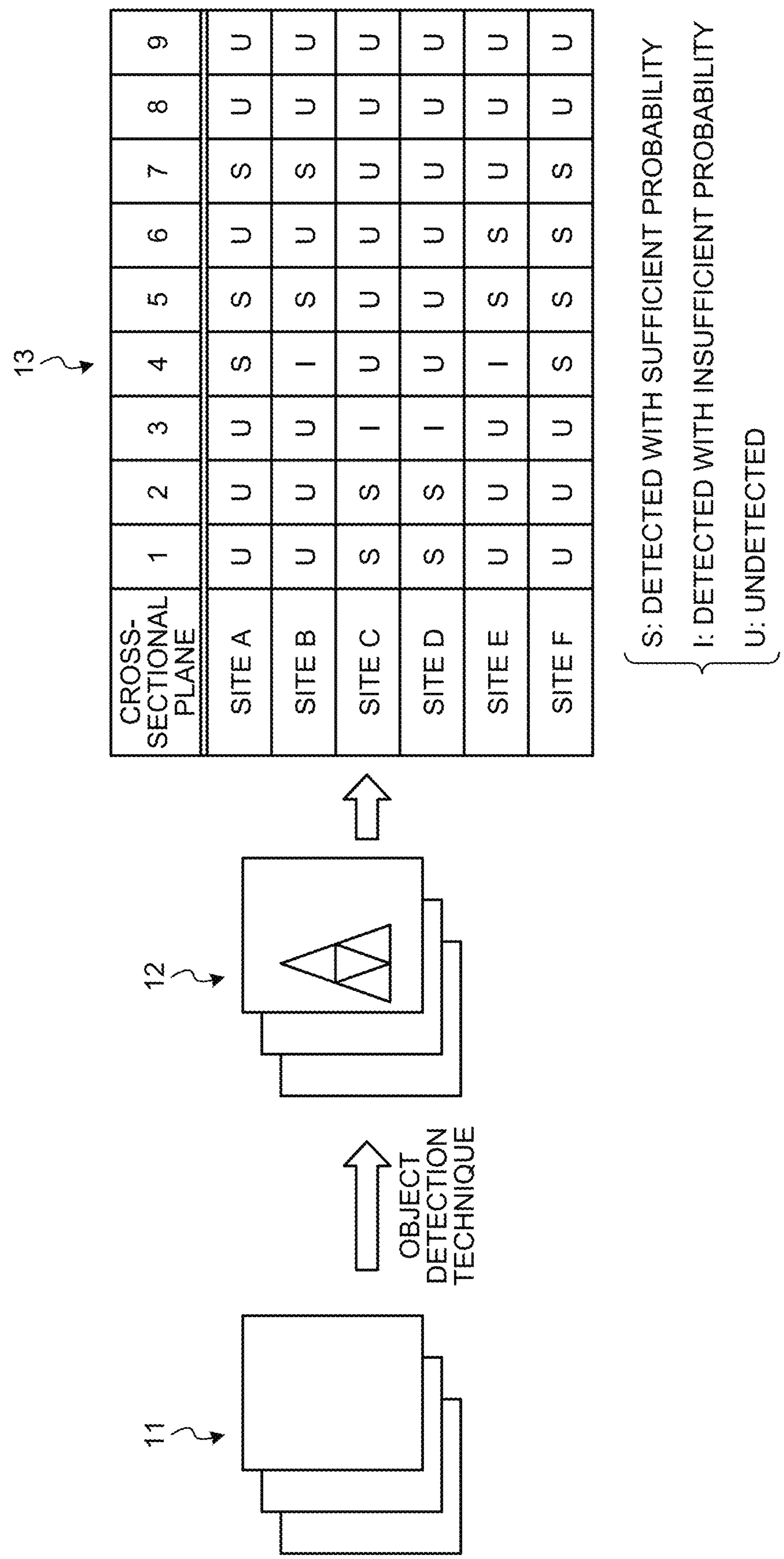
FIG. 2 is a drawing illustrating an example of a site detection map based on an object detection technique.

FIG. 2 is a drawing illustrating an example of the site detection map based on the object detection technique. As illustrated in FIG. 2, the examination assisting apparatus 100 performs a site detecting process by applying the object detection technique using machine learning, on a plurality of ultrasound examination images 11 taken of the examined subject by performing a scan thereon so as to obtain detection results 12. As for the scanning direction, the scan may be performed in a forward direction, for example. However, the scan may be performed in a reverse direction. On the basis of the detection results 12, the examination assisting apparatus 100 generates and displays a site detection map 13 in which detection results of a plurality of sites ("sites A to F") included in the examined subject are kept in correspondence with "cross sectional planes 1 to 9" of the scan. In this situation, the detection results are represented by probabilities of the sites. In the site detection map 13, each of the sites detected with a sufficient probability is indicated with "S", while each of the sites detected with an insufficient probability is indicated with "I", and each of the undetected sites is indicated with "U".

Next, a configuration of the examination assisting apparatus 100 will be explained. As illustrated in FIG. 1, the examination assisting apparatus 100 includes a probe 110, a display unit 111, an operating unit 112, a storage unit 120, and a controlling unit 130. In addition to the functional units illustrated in FIG. 1, the examination assisting apparatus 100 may include any of various types of functional units included in known computers, e.g., functional units of various types of input devices and audio output devices.

The probe 110 is an example of a probing device that emits an ultrasound wave toward the examined subject and receives an ultrasound wave reflected on the inside of the examined subject. As the probe 110, for example, it is possible to use any of various types of probes such as linear-type, convex-type, and sector-type probes. Further, for example, the probe 110 is capable of using an ultrasound wave with a frequency in the range from 2 MHz to 20 MHz approximately. The probe 110 outputs reception data to the controlling unit 130.

Figure 3:
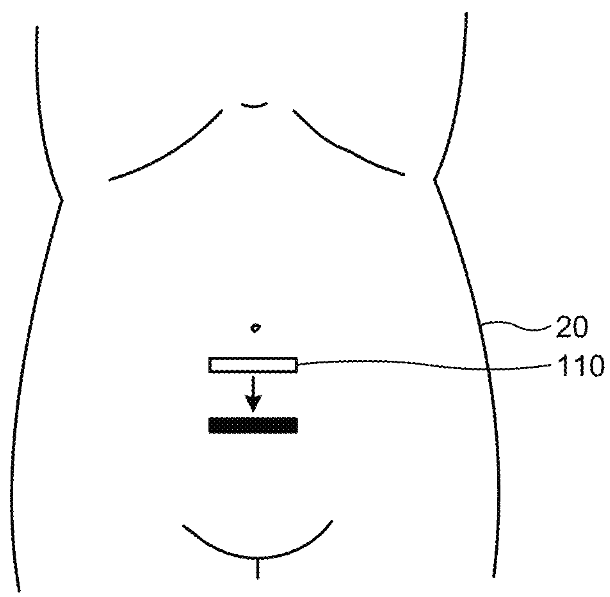
FIG. 3 is a drawing illustrating an example of scanning methods implemented by a probe.

Next, scanning methods implemented by the probe will be explained, with reference to FIGS. 3 to 6. FIG. 3 is a drawing illustrating an example of the scanning methods implemented by the probe. FIG. 3 illustrates an example of a slide scan. The slide scan uses a scanning method by which, while being held vertically or horizontally, the probe 110 is moved parallel to a mother's body 20 so as to slide in an orthogonal direction without changing the angle thereof.

Figure 4:
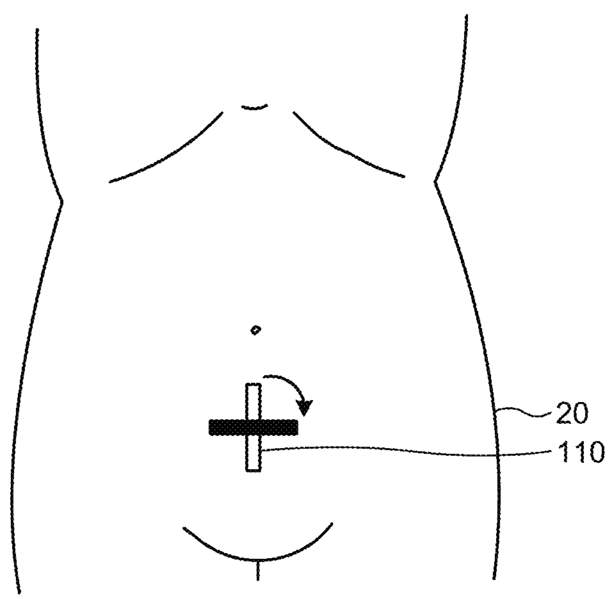
FIG. 4 is a drawing illustrating another example of the scanning methods implemented by the probe.

FIG. 4 is a drawing illustrating another example of the scanning methods implemented by the probe. FIG. 4 illustrates an example of a rotation scan. The rotation scan uses a scanning method by which, while using the center of the probe 110 as an axis, the probe 110 is rotated without changing the rendering position with respect to the mother's body 20.

Figure 5:
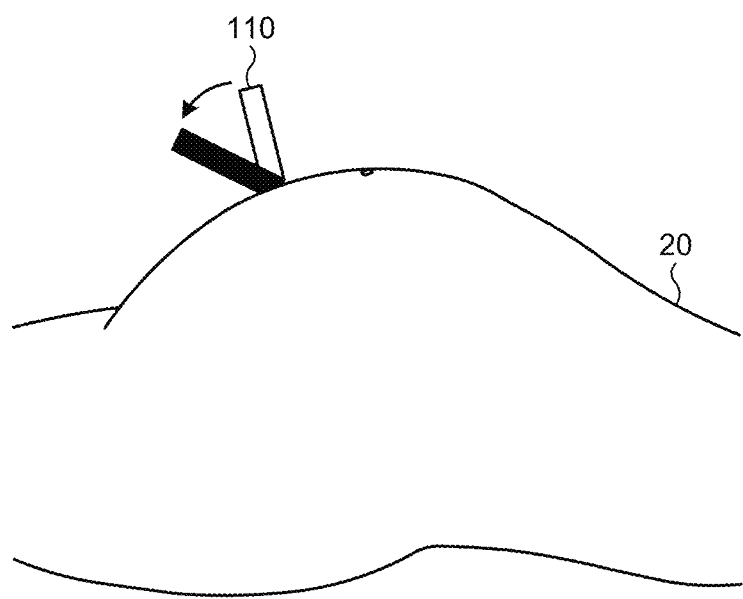
FIG. 5 is a drawing illustrating yet another example of the scanning methods implemented by the probe.

FIG. 5 is a drawing illustrating yet another example of the scanning methods implemented by the probe. FIG. 5 illustrates an example of a fan-shaped scan. The fan-shaped scan uses a scanning method by which, while the position of the probe 110 is maintained with respect to the mother's body 20, a user swings the probe 110 in a fan-shaped region by using his/her wrist.

Figure 6:
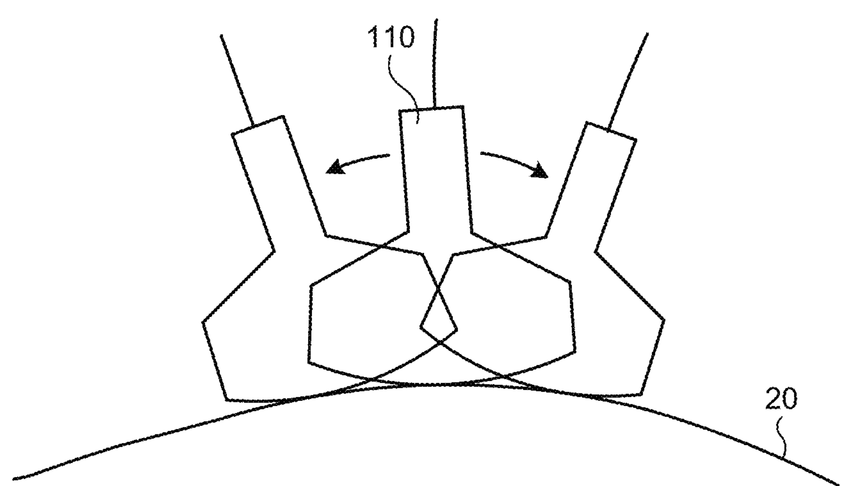
FIG. 6 is a drawing illustrating yet another example of the scanning methods implemented by the probe.

FIG. 6 is a drawing illustrating yet another example of the scanning methods implemented by the probe. FIG. 6 illustrates an example of a pendulum scan. The pendulum scan uses a scanning method by which, while the probe 110 of a convex-type is being used, the probe 110 is swung in left-and-right directions with respect to the mother's body 20, by using the semicircular curved surface in a convex shape.

Returning to the description of FIG. 1, the display unit 111 is a display device used for displaying various types of information. For example, the display unit 111 is realized as a display device by using a liquid crystal display monitor or the like. The display unit 111 displays various types of screens such as a display screen input thereto from the controlling unit 130.

The operating unit 112 is an input device that receives various types of operations from the user of the examination assisting apparatus 100. For example, the operating unit 112 is realized as an input device by using a keyboard, a mouse, and/or the like. The operating unit 112 outputs an operation input thereto by the user to the controlling unit 130, as operation information. Alternatively, the operating unit 112 may be realized as an input device by using a touch panel or the like. Further, the display device of the display unit 111 and the input device of the operating unit 112 may integrally be formed.

The storage unit 120 is realized by using a storage device, e.g., a semiconductor memory element such as a Random Access Memory (RAM) or a flash memory, or a hard disk, an optical disk, or the like. The storage unit 120 includes an image storage unit 121, an object data storage unit 122, a learning model storage unit 123, and a site detection data storage unit 124. Further, the storage unit 120 stores therein information used in processes performed by the controlling unit 130.

The image storage unit 121 stores therein a plurality of ultrasound examination images on the basis of the reception data input from the probe 110. In this situation, the plurality of ultrasound examination images may be, for example, represented by a moving image having a plurality of frames. In the explanation below, the plurality of ultrasound examination images may be referred to as a "moving image", while an image in a frame of the moving image may be referred to as an "examination image" or an "ultrasound examination image".

The object data storage unit 122 stores therein object data indicating the structure of an object serving as an examined subject. As the object data, it is possible to use, for example, rule-based data estimated by using the current position of the probe 110 and a relationship between a preceding frame and a following frame, or the like. Alternatively, as the object data, it is also acceptable to use data based on a three-dimensional model or the like based on a manual input or a design drawing. In other words, the object data may be expressed as a set $R_t$ made up of sites that are supposed to be rendered in an examination image $m_t$ taken at a time t, the set $R_t$ having been obtained by using a certain method. Accordingly, in the explanation below, the set $R_t$ made up of the sites that are supposed to be rendered in the examination image $m_t$ taken at the time t may also be referred to as object data $R_t$. Further, a time period of times t corresponding to examination images $m_t$ of which the object data $R_t$ is present is expressed as a time set $T_R$. A set made up of the examination images $m_t$ corresponding to the time set $T_R$ will be expressed as all examination images M. In other words, the object data storage unit 122 stores therein the time set $T_R$ together with the object data $R_t$. The object data $R_t$ corresponding to the time set $T_R$ will be expressed as object data R.

With regard to the object serving as the examined subject, the learning model storage unit 123 stores therein a learning model obtained by learning a plurality of elements h related to a structure H of the object. The learning model is obtained by learning, in advance, the elements h of the structure H of the object, by using an object detection algorithm such as YOLO, a Single Shot MultiBox Detector (SSD), a Faster-Recurrent Neural Network (RNN), or the like. For example, the learning model stores therein various types of parameters (weight coefficients) of a neural network, or the like.

With respect to each of the examination images $m_t$, the site detection data storage unit 124 stores therein site detection data, which is data obtained by detecting the elements h of the structure H of the object by using the learning model. It is possible to express the site detection data as a set $D_t$ made up of sites (elements h) rendered in the examination image $m_t$ taken at the time t. Accordingly, in the explanation below, the set $D_t$ made up of the sites rendered in the examination image $m_t$ taken at the time t may also be expressed as site detection data $D_t$. Further, the site detection data $D_t$ may also be expressed as a probability map $D(h,t)$, when a focus is placed on a set made up of probabilities $P\_h(m\_t)$ of the sites (the elements h) rendered in the examination image $m_t$ taken at the time t. In other words, the probability map $D(h,t)$ is a set made up of probabilities $P\_h(m\_t)$ of the sites (the elements h) rendered in the examination image $m_t$ taken at the time t. That is to say, the probability map $D(h,t)$ is an example of the site detection map. The site detection data $D_t$ corresponding to the time set $T_R$ will be expressed as site detection data D.

For example, the controlling unit 130 is realized as a result of a Central Processing Unit (CPU), a Micro Processing Unit (MPU), or the like executing a program stored in a storage device provided on the inside thereof, while using a RAM as a work area. Alternatively, the controlling unit 130 may be realized by using an integrated circuit, e.g., an Application Specific Integrated Circuit (ASIC), a Field Programmable Gate Array (FPGA), or the like. The controlling unit 130 includes an obtaining unit 131, a judging unit 132, a detecting unit 133, and a display controlling unit 134 and realizes or executes information processing functions or actions described below. Possible internal configurations of the controlling unit 130 are not limited to the configuration illustrated in FIG. 1. The controlling unit 130 may have a different configuration as long as it is possible to implement the information processing processes described below.

When being instructed to start obtaining a moving image, the obtaining unit 131 starts obtaining the reception data from the probe 110. On the basis of the obtained reception data, the obtaining unit 131 starts generating the moving image. In other words, the obtaining unit 131 starts obtaining the moving image. The examination images based on the reception data are obtained by calculating a distance by using a time period between when an ultrasound wave is emitted and when a reflected wave returns. For example, it is possible to use any of various types of examination images such as B-mode, M-mode, and color Doppler images. Further, when the obtained moving image has a section in which the scanning direction goes backward due to a movement of the fetus or the like, for example, the obtaining unit 131 eliminates one or more frames corresponding to the backward part by comparing the frames of the moving image with one another. The obtaining unit 131 stores the obtained moving image into the image storage unit 121 and also outputs the obtained moving image to the judging unit 132.

Figure 7:
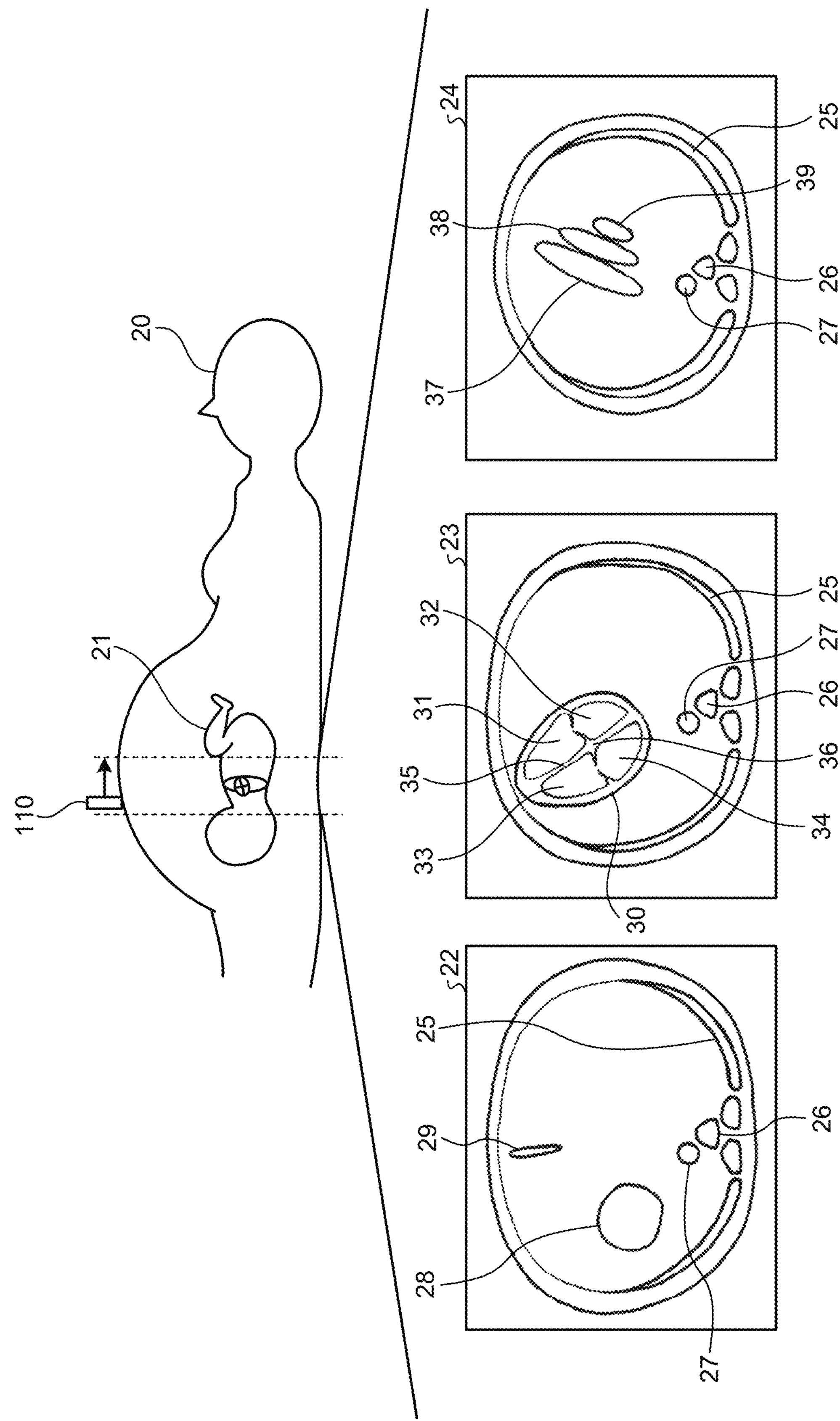
FIG. 7 is a drawing illustrating an example of a process of obtaining ultrasound examination images.

Next, the process of obtaining the moving image, i.e., the process of obtaining the plurality of ultrasound examination images, will be explained with reference to FIG. 7. FIG. 7 is a drawing illustrating an example of the process of obtaining the ultrasound examination images. In the example in FIG. 7, the examination images (the ultrasound examination images) are obtained by scanning the abdomen of the mother's body 20 with the probe 110, with regard to a fetus 21 inside the mother's body 20. For example, the probe 110 is operated by a medical doctor to continuously perform a scan starting from the vicinity of the stomach of the fetus 21 toward the upper section of the heart. As the examination images in this situation, examination images 22 to 24 are obtained as examples of examination images before and after the heart and an example of an examination image of the heart. The examination image 22 renders ribs 25, the spine 26, the descending aorta 27, the stomach 28, and the umbilical vein 29.

The examination image 23 renders ribs 25, the spine 26, the descending aorta 27, and the heart 30. Further, the examination image 23 also renders sites of the internal structure of the heart 30, namely, the right ventricle 31, the right atrium 32, the left ventricle 33, the left atrium 34, the interventricular septum 35, and the crux cordis 36. In this situation, the heart 30 corresponds to the structure H of an object, i.e., a set made up of structures of the heart. Further, the right ventricle 31, the right atrium 32, the left ventricle 33, the left atrium 34, the interventricular septum 35, and the crux cordis 36 correspond to the elements h. The examination image 24 renders ribs 25, the spine 26, the descending aorta 27, the pulmonary artery 37, the ascending aorta 38, and the superior vena cava 39. In the present embodiment, with respect to the time period (the time set T_R) during which the heart is rendered in the examination images after the scan is started, probabilities are calculated and displayed with respect to each of the sites, by comparing the object data R with the site detection data D. The examination images 22 to 24 in FIG. 7 are illustrated so that the sites are easy to see for explanation purposes; however, in actual examination images, the sites would not be clearly displayed in this manner.

Returning to the description of FIG. 1, the judging unit 132 judges whether or not the structure H (the heart) of the object serving as the examined subject is rendered in the examination image m_t, by using the relationship between the preceding frame and the following frame in the moving image. When having received the input of the moving image from the obtaining unit 131, the judging unit 132 extracts an examination image m_t in one frame from the input moving image. By making use of the fact that the heart has large pulsating movements, the judging unit 132 calculates a score (rule_score) corresponding to the pulsation by using Expression (1) presented below. In other words, the judging unit 132 calculates the score corresponding to the pulsation on the basis of a difference between the frames in the moving image.

$$(\text{rule\_score}) = \sum_{x,y} (\text{m\_t}'(x, y) - \text{m\_t}(x, y))^2 \quad (1)$$

In Expression (1), x denotes the vertical axis of the screen, whereas y denotes the horizontal axis of the screen. Further, m_t(x,y) denotes a pixel at coordinates (x,y) in the examination image (the frame) taken at the time t. The entirety of Expression (1) expresses calculating, as the score, a sum of differences between an examination image taken at a time earlier than the time t by a time period "a" and the examination image taken at the time t. The higher the score is, the larger change is exhibited in the examination images during the time period "a", i.e., the heart is pulsating. The value t' denotes t-a, which is a value obtained by subtracting the predetermined difference "a" from "t". The difference "a" denotes approximately "1 to 20", for example. In a 40-fps moving image, because the unit of time is $1/40$ seconds, the difference "a" is in the range "from $1/40$ seconds to $1/2$ seconds" approximately.

The judging unit 132 judges whether or not the examination image m_t renders the structure H (the heart) of the object serving as the examined subject, by judging whether or not the calculated score exceeds a threshold value k_r set in advance. The threshold value k_r may be an arbitrary value and may be a value such as "3.0", for example. When having determined that the examination image m_t renders the structure H (the heart) of the object serving as the examined subject, the judging unit 132 calculates the set R_t made up of the sites supposed to be rendered in the examination image m_t taken at the time t, as expressed in Expression (2) presented below. On the contrary, when having determined that the examination image m_t does not render the structure H (the heart) of the object serving as the examined subject, the judging unit 132 calculates the object data R_t as expressed in Expression (3) presented below (where R_t=an empty set). In Expression (2), the object data R_t rendering the structure H of the object is calculated on the basis of the six elements h; however, it is acceptable to calculate the object data R_t on the basis of an arbitrary number of elements h.

$$R\_t = \{\text{right ventricle, right atrium, left ventricle, left atrium, interventricular septum, crux cordis}\} \quad (2)$$

$$R\_t = \emptyset \quad (3)$$

Further, when the object data R_t is calculated as expressed in Expression (2), the judging unit 132 adds the time t to the time set T_R. The judging unit 132 stores the calculated object data R_t and the time set T_R into the object data storage unit 122. Further, the judging unit 132 outputs the extracted examination image m_t to the detecting unit 133.

Further, when having received the input of an end judging instruction from the detecting unit 133, the judging unit 132 judges whether or not the moving image has finished. In other words, the judging unit 132 judges whether or not the extracted examination image m_t was the final frame of the moving image. When having determined that the moving image has not finished, the judging unit 132 advances the time t by 1, extracts the following examination image m_t from the moving image, and repeats the process of judging whether or not the structure H (the heart) of the object is rendered. On the contrary, when having determined that the moving image has finished, the judging unit 132 outputs a generation instruction to the display controlling unit 134.

When having received the input of the examination image m_t from the judging unit 132, the detecting unit 133 refers to the learning model storage unit 123 and performs a process of detecting the elements h (the sites) of the structure H (the heart) of the object on the input examination image m_t, by using the learning model. In other words, the detecting unit 133 calculates site detection data D_t, which is a set D_t made up of the sites (the elements h) rendered in the examination image m_t, by using Expression (4) presented below.

$$D\_t = \{h \mid P\_h(m\_t) \text{ is equal to or larger than the threshold value } k\_d\} \quad (4)$$

In Expression (4), P_h denotes a probability of the position of the element h that is calculated when the element h is detected by using the learning model. The threshold value k_d is a threshold value used for judging the detection of the element h with respect to the probability of the position of the element h. In other words, by using Expression (4), the detecting unit 133 calculates a detection result of each of the elements h (the sites) from the examination image m_t, as the site detection data D_t. In this situation, the threshold value k_d may be an arbitrary value and may be a value such as "3.0", for example. By adjusting the value of the threshold value "k_d", it is possible to set acuteness of the detection in a range from "an element being completely missing" to "deviation from normal data".

Further, by placing a focus on the probability P_h, it is possible to express Expression (4) as a probability map D(h,t) by using Expression (5) presented below.

$$D(h,t)=\begin{cases}0 & (P\_h(m\_t)<k\_d)\\ P\_h(m\_t) & (P\_h(m\_t)\geqq k\_d)\end{cases}\quad(5)$$

The probability P_h and the threshold value k_d in Expression (5) are the same as those in Expression (4). The detecting unit 133 stores the calculated site detection data D_t into the site detection data storage unit 124 and also outputs an end judging instruction to the judging unit 132.

In other words, the detecting unit 133 performs the site detecting process that uses the object detection technique on each of the plurality of ultrasound examination images selected by the judging unit 132.

When having received the input of the generation instruction from the judging unit 132, the display controlling unit 134 refers to the object data storage unit 122 and obtains the time set T_R. Further, the display controlling unit 134 refers to the site detection data storage unit 124 and obtains the site detection data D corresponding to the time set T_R. On the basis of the time set T_R and the site detection data D, the display controlling unit 134 generates a site detection map corresponding to all the examination images M. In this situation, in a frame corresponding to such a time t that is not included in the time set T_R, because there is supposed to be no site of the examined subject, the display controlling unit 134 indicates the site as "undetected". Further, when generating the site detection map, the display controlling unit 134 may refer to the object data R in the object data storage unit 122.

In other words, on the basis of the time set T_R and the site detection data D, the display controlling unit 134 generates, by using Expression (5), the probability map D(h,t), which is a site detection map in which detection results of the sites (the elements h) in each of the examination images m_t are arranged along the scanning direction (the direction of the times t). The display controlling unit 134 outputs the generated site detection map to the display unit 111 and causes the display unit 111 to display the site detection map.

While generating the site detection map, when the data corresponding to a certain site in the site detection data D_t representing the detection results is consecutively in the state of being undetected or exhibiting a probability lower than a predetermined value for a time period equal to or longer than a predetermined number of times t, the display controlling unit 134 displays the part corresponding to such a site in a highlighted manner. In other words, when a certain site remains undetected in examination images over a certain span, the display controlling unit 134 is capable of presenting that there is a high possibility of an abnormality, by displaying such a section of the site detection map corresponding to the site in the highlighted manner.

Further, when there is an examination image having a detection result in which all of the plurality of sites are indicated as undetected, the display controlling unit 134 is capable of presenting that there is a problem in the image quality of the examination image by displaying, in a highlighted manner, such a section of the site detection map that corresponds to the examination image. Further, in accordance with the indication of being undetected and the probabilities of the detected sites, for example, the display controlling unit 134 is also capable of presenting display corresponding to the probabilities, by displaying the data in such a manner that the higher the probability is, the more noticeable color for the user is used for the display of the data, for example. Further, when any one of the detection results is designated in the site detection map, the display controlling unit 134 displays an examination image corresponding to the designated detection result. Further, when detection results in which all of the plurality of sites are indicated as undetected are consecutively observed in the scanning direction (the direction of the times t), the display controlling unit 134 displays information indicating that the scan is defective.

In other words, on the basis of the detection results, the display controlling unit 134 displays the site detection map in which the detection result of each of the plurality of sites included in the examined subject is kept in correspondence with the scan. Further, among one or more of the sites of which the detection result is indicated as undetected and one or more of the sites of which the detection result exhibits a probability lower than a predetermined value, when at least one of such sites is consecutively observed in the scan for a time period equal to or longer than a predetermined length of time, the display controlling unit 134 displays, in a highlighted manner, the part of the site detection map corresponding to the site. In this situation, the predetermined length of time may be a time period in the scan direction corresponding to the time t=6 or longer, for example. Further, with respect to a detection result in which all of the plurality of sites are indicated as undetected, the display controlling unit 134 displays, in a highlighted manner, the part of the site detection map corresponding to the detection result. Further, the display controlling unit 134 displays the detection results in different modes in accordance with the indication of being undetected and the probabilities of the detection results. Further, when any one of the detection results is designated in the site detection map, the display controlling unit 134 displays an ultrasound examination image corresponding to the designated detection result. Further, when detection results in which all of the plurality of sites are indicated as undetected are consecutively observed, the display controlling unit 134 displays information indicating that the scan is defective.

Next, site detection maps exhibiting various patterns will be explained, with reference to FIGS. 8 to 12. FIG. 8 is a drawing illustrating an example of the site detection map exhibiting a normal pattern. A site detection map 40 illustrated in FIG. 8 is the example of the site detection map exhibiting the normal pattern. The site detection map 40 illustrated in FIG. 8 indicates values of the probability map D(h,t) while the vertical axis expresses the sites serving as the elements h, whereas the horizontal axis expresses the cross-sectional planes (the examination images) corresponding to the times t. The site detection map 40 indicates that "sites A to F" are detected with sufficient probabilities over a certain number of cross-sectional planes (examination images). As for the probabilities of the sites on the cross-sectional planes, each of the sites detected with a sufficient probability is indicated with "S", while each of the sites detected with an insufficient probability is indicated with "I", and each of the undetected sites is indicated with "U", similarly to the site detection map 13 illustrated in FIG. 2. Further, on "cross-sectional plane 6", none of the sites is detected. However, on the preceding and the following cross-sectional planes, certain sites are detected. Accordingly, there is a high possibility that the problem lies in the image quality of the examination image on "cross-sectional plane 6", rather than an abnormality in the examined subject.

For this reason, by displaying a box 41 so as to display the column of "cross-sectional plane 6" in a highlighted manner, for example, the examination assisting apparatus 100 is able to provide assistance for the examination.

Figure 9:
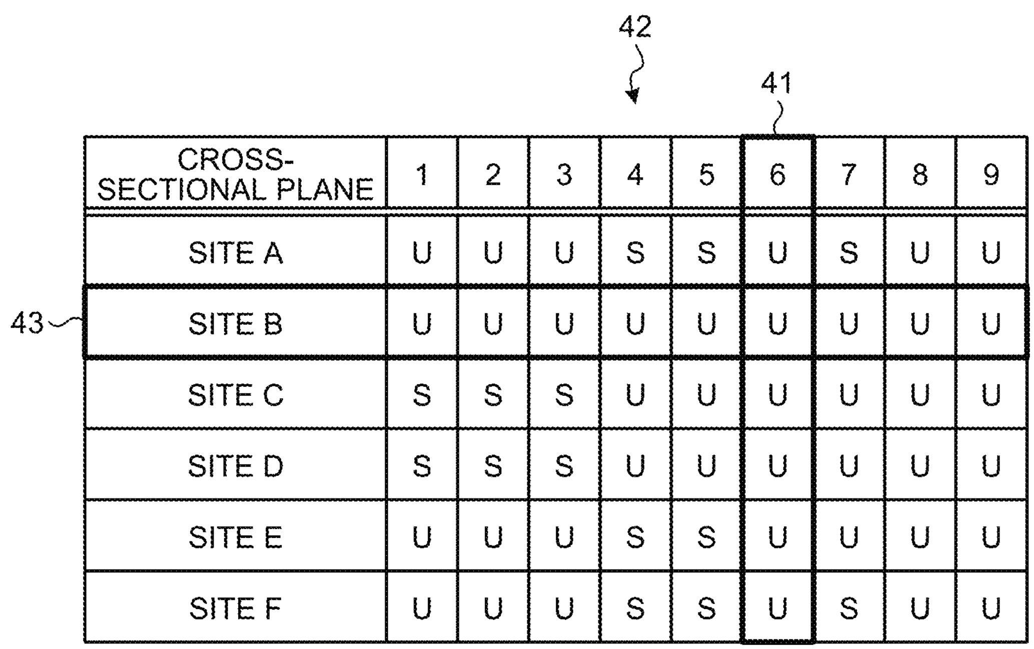
FIG. 9 is a drawing illustrating an example of the site detection map exhibiting an abnormal pattern.

FIG. 9 is a drawing illustrating an example of the site detection map exhibiting an abnormal pattern. A site detection map 42 illustrated in FIG. 9 is the example of the site detection map exhibiting the abnormal pattern. The site detection map 42 illustrated in FIG. 9 indicates values of the probability map D(h,t) while the vertical axis expresses the sites serving as the elements h, whereas the horizontal axis expresses the cross-sectional planes (the examination images) corresponding to the times t. The site detection map 42 indicates that "site A" and "sites C to F" are detected with sufficient probabilities over a certain number of cross-sectional planes (examination images) but that "site B" is not detected over a certain number of cross-sectional planes (examination images). Accordingly, in the site detection map 42, there is a high possibility that an abnormality relevant to "site B" may be present. For this reason, the examination assisting apparatus 100 is able to provide assistance for the examination by, for example, displaying a box 43 so as to display the row of "site B" in a highlighted manner. Further, the examination assisting apparatus 100 may display, in a highlighted manner, a row corresponding to a site on which a focus is placed during the examination. Further, in the site detection map 42, by displaying the box 41 for the "cross-sectional plane 6" so as to display the column of "cross-sectional plane 6" in a highlighted manner similarly to the site detection map 40, it is possible to provide assistance for the examination.

FIG. 10 is a drawing illustrating another example of the site detection map exhibiting an abnormal pattern. A site detection map 44 illustrated in FIG. 10 is the example of the site detection map exhibiting the abnormal pattern that is different from that in the site detection map 42. The site detection map 44 illustrated in FIG. 10 indicates values of the probability map D(h,t) while the vertical axis expresses the sites serving as the elements h, whereas the horizontal axis expresses the cross-sectional planes (the examination images) corresponding to the times t. The site detection map 44 indicates that "site A" and "sites C to F" are detected with sufficient probabilities over a certain number of cross-sectional planes (examination images) but that "site B" is detected with low probabilities over a certain number of cross-sectional planes (examination images). Accordingly, in the site detection map 44, there is a high possibility that an abnormality relevant to "site B" may be present, because the shape and the texture or the like of "site B" are different from those in normal situations. For this reason, the examination assisting apparatus 100 is able to provide assistance for the examination by, for example, displaying a box 45 so as to display the row of "site B" in a highlighted manner. Further, in the site detection map 44, by displaying the box 41 for "cross-sectional plane 6" so as to display the column of "cross-sectional plane 6" in a highlighted manner similarly to the site detection map 40, it is possible to provide assistance for the examination.

FIG. 11 is a drawing illustrating an example of the site detection map exhibiting an undeterminable pattern. A site detection map 46 illustrated in FIG. 11 is the example of the site detection map exhibiting the undeterminable pattern. The site detection map 46 illustrated in FIG. 11 indicates values of the probability map D(h,t) while the vertical axis expresses the sites serving as the elements h, whereas the horizontal axis expresses the cross-sectional planes (the examination images) corresponding to the times t. The site detection map 46 indicates that certain sites are detected on "cross-sectional plane 3" and "cross-sectional plane 4" but that no site is detected on the other cross-sectional planes. When the number of cross-sectional planes on which certain sites are detected is significantly small as observed in this example, the examination assisting apparatus 100 judges that the detection results are undeterminable and, for example, displays, on the display unit 111, information indicating that the scan performed by the probe 110 is defective.

FIG. 12 is a drawing illustrating another example of the site detection map exhibiting an undeterminable pattern. A site detection map 47 illustrated in FIG. 12 is the example of the site detection map exhibiting the undeterminable pattern different from that in the site detection map 46. The site detection map 47 illustrated in FIG. 12 indicates values of the probability map D(h,t) while the vertical axis expresses the sites serving as the elements h, whereas the horizontal axis expresses the cross-sectional planes (the examination images) corresponding to the times t. The site detection map 47 indicates that cross-sectional planes on which none of the sites is detected are consecutively observed in "cross-sectional plane 5" and "cross-sectional plane 6". In this manner, when cross-sectional planes on which the majority of the sites are not detected successively continue, the examination assisting apparatus 100 judges that the detection results are undeterminable and displays, on the display unit 111, information indicating that the scan performed by the probe 110 is defective, for example.

Figure 13:
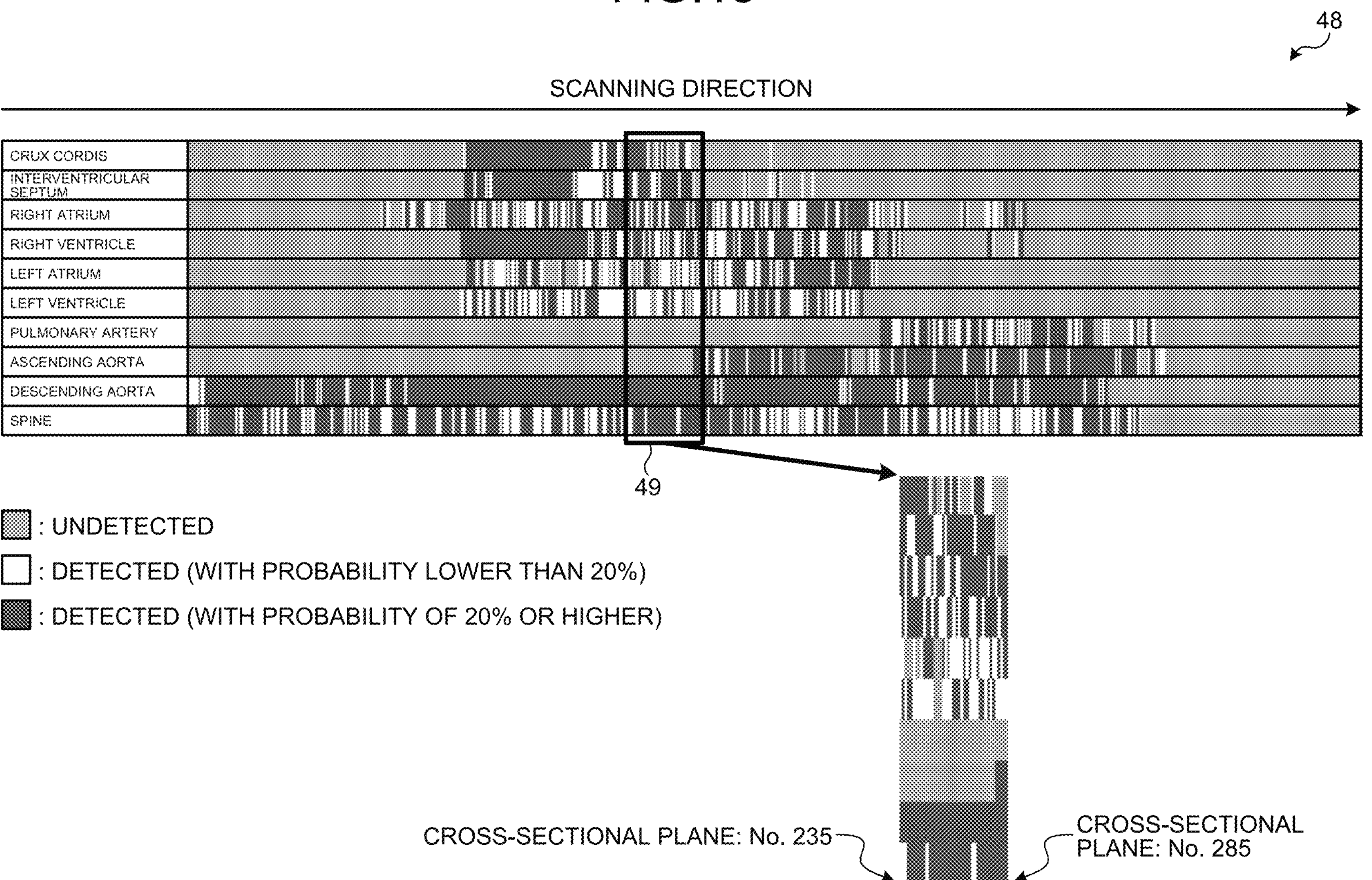
FIG. 13 is a drawing illustrating an example of the site detection map.

Next, examples of a site detection map, ultrasound examination images, and site detection results from the ultrasound examination images will be explained by using an example in which a fetal heart is used as an examined subject, with reference to FIGS. 13 to 18. FIG. 13 is a drawing illustrating an example of the site detection map. A site detection map 48 illustrated in FIG. 13 indicates values of the probability map D(h,t) while the vertical axis expresses the elements h, whereas the horizontal axis expresses the time t. The site detection map 48 indicates values of the probability map D(h,t) by using a gray scale, instead of the symbols "S", "I", and "U" used in FIGS. 8 to 12. For example, the site detection map 48 indicates the detection results at three levels, namely undetected, detected (with a probability lower than 20%), and detected (with a probability of 20% or higher). Alternatively, it is also acceptable to configure the site detection map 48 so as to display "undetected" in gray and display "detected (with a probability lower than 20%)" and "detected (with a probability of 20% or higher)" in different colors such as white and blue, for example. Next, by extracting cross-sectional planes Nos. 235 to 285 indicated with a box 49, ultrasound examination images and site detection results will be explained.

Figure 14:
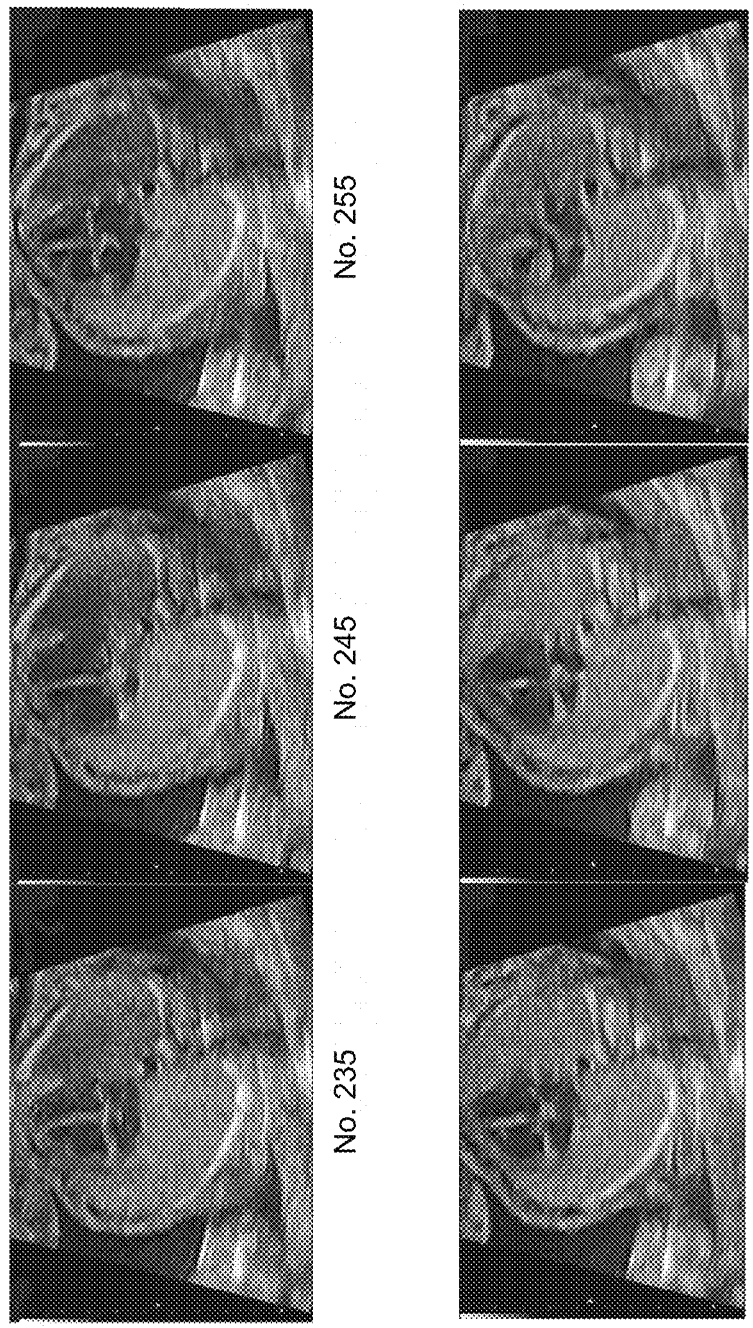
FIG. 14 is a drawing illustrating examples of ultrasound examination images.

FIG. 14 is a drawing illustrating examples of ultrasound examination images. Among the extracted cross-sectional planes in FIG. 13, FIG. 14 illustrates ultrasound examination images corresponding to Nos. 235, 245, 255, 265, 275, and 285. In these ultrasound examination images, shadows are observed over the cross-sectional planes corresponding to Nos. 245 and 255.

Figure 15:
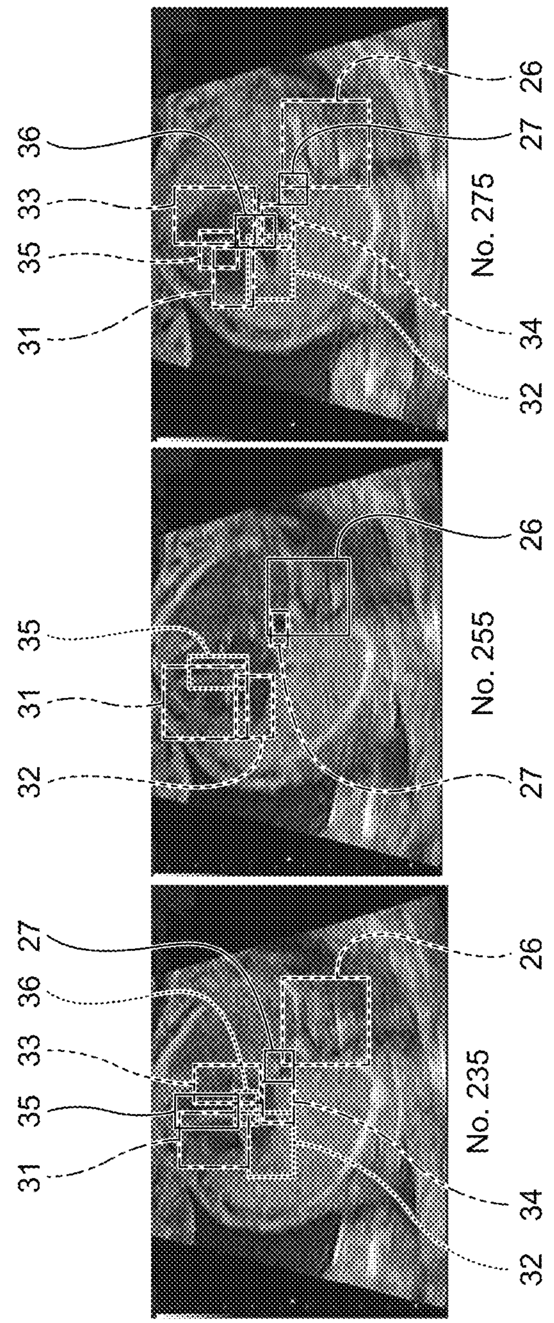
FIG. 15 is a drawing illustrating examples of site detection results.

FIG. 15 is a drawing illustrating examples of site detection results. Among the ultrasound examination images in FIG. 14, FIG. 15 illustrates site detection results corresponding to Nos. 235, 255, and 275. In No. 235, the spine 26, the descending aorta 27, the right ventricle 31, the right atrium 32, the left ventricle 33, the left atrium 34, the interventricular septum 35, and the crux cordis 36 are detected. In No. 255, the spine 26, the descending aorta 27, the right ventricle 31, the right atrium 32, and the interventricular septum 35 are detected. In other words, in No. 255, because of the shadows, the left ventricle 33, the left atrium 34, and the crux cordis 36 are not detected. In No. 275, the spine 26, the descending aorta 27, the right ventricle 31, the right atrium 32, the left ventricle 33, the left atrium 34, the interventricular septum 35, and the crux cordis 36 are detected.

Accordingly, among the cross-sectional planes corresponding to Nos. 235 to 285 that represent the sections extracted from the site detection map 48, the undetected sites in No. 255 are detected on the cross-sectional planes preceding and following No. 255, it is understood that the sites are normal. In other words, it is understood that the shadows on cross-sectional planes No. 245 and 255 are caused by the scan performed by the probe 110. Further, the examination assisting apparatus 100 may display, in a real-time manner, boxes indicating detection results of the sites as illustrated in FIG. 15, within the ultrasound examination images for the monitor that are displayed on the display unit 111 during the scan performed by the probe 110. Further, the examination assisting apparatus 100 may display labels indicating the names of the sites or the like, for example, with the boxes indicating the detection results of the sites illustrated in FIG. 15.

Figure 16:
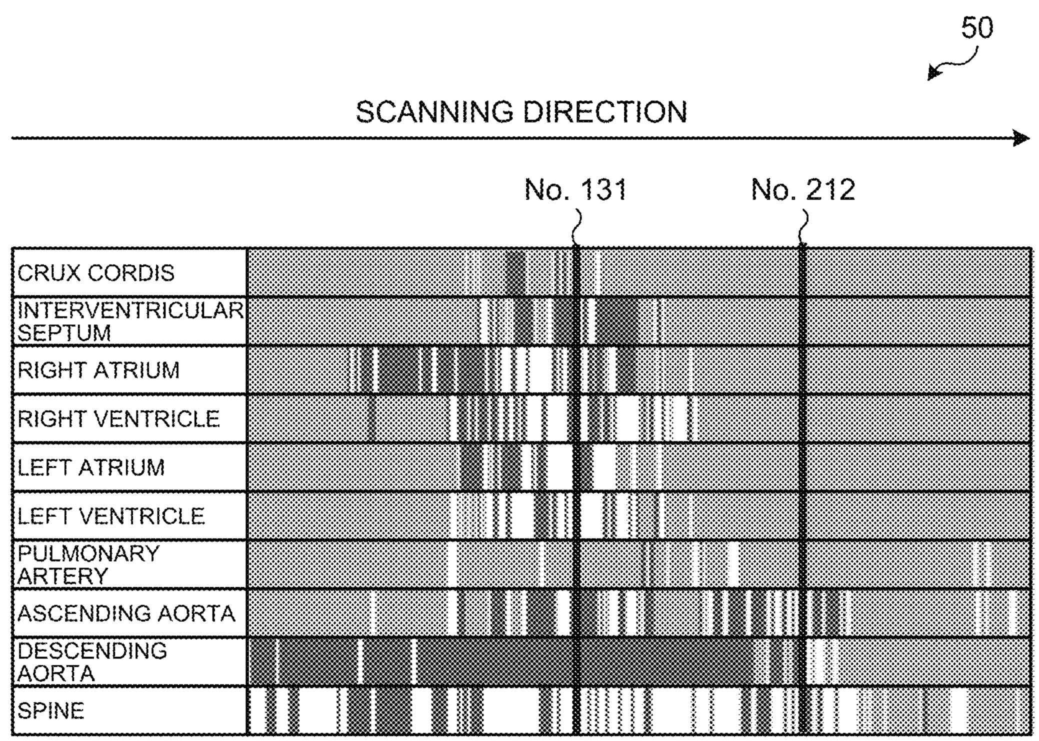
FIG. 16 is a drawing illustrating another example of the site detection map.

FIG. 16 is a drawing illustrating another example of the site detection map. Similarly to the site detection map 48 illustrated in FIG. 13, a site detection map 50 illustrated in FIG. 16 indicates values of the probability map D(h,t) while the vertical axis expresses the elements h, whereas the horizontal axis expresses the time t. The site detection map 50 indicates detection results with tetralogy of Fallot, which is a typical congenital heart disease. From the site detection map 50, it is observed that the crux cordis 36 is missing (a hole in the interventricular septum 35) and the pulmonary artery 37 is missing, which reflect symptoms of tetralogy of Fallot. Examples of the cross-sectional planes corresponding to the missing crux cordis 36 include No. 131. Examples of the cross-sectional planes corresponding to the mixing pulmonary artery 37 include no. 212.

Figure 17:
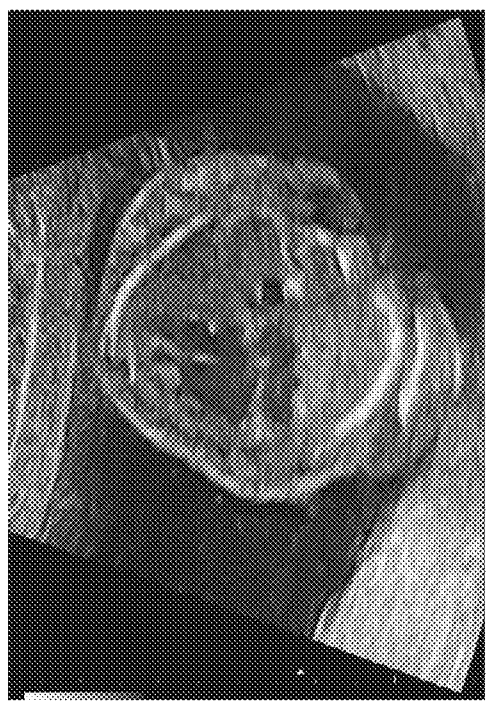
FIG. 17 is a drawing illustrating other examples of the ultrasound examination images.

FIG. 17 is a drawing illustrating other examples of ultrasound examination images. FIG. 17 illustrates the ultrasound examination images corresponding to Nos. 131 and 212 in FIG. 16. From No. 131, it is observed that the crux cordis 36 is missing. From No. 212, it is observed that the pulmonary artery 37 is narrowed due to a stenosis. As for relationships between abnormal sites and diseases, for example, when the crux cordis 36 is an abnormal site, corresponding diseases are a complete/incomplete atrioventricular septal defect and tetralogy of Fallot (TOF). As another example, when the crux cordis 36 and the interventricular septum 35 are abnormal sites, a corresponding disease is a single left ventricle defect. As yet another example, when the left atrium 34 is an abnormal site, corresponding diseases are pulmonary atresia with intact ventricular septum and Ebstain anomaly. As yet another example, when the pulmonary artery 37 is an abnormal site, a corresponding disease is mitral atresia. As yet another example, when the descending aorta 27 and the spine 26 are abnormal sites, corresponding diseases are transposition of the great arteries, truncus arteriosus, and tetralogy of Fallot (TOF).

FIG. 18 is a drawing illustrating other examples of the site detection results. FIG. 18 illustrates the site detection results regarding Nos. 131 and 212 in FIG. 17. In No. 131, the descending aorta 27, the right ventricle 31, the right atrium 32, the left ventricle 33, the left atrium 34, the interventricular septum 35, and the ascending aorta 38 are detected. In contrast, in No. 131, the crux cordis 36 is missing and therefore not detected. In No. 212, the descending aorta 27 and the ascending aorta 38 are detected. In contrast, in No. 212, the pulmonary artery 37 is narrowed due to the stenosis and is therefore not detected. In other words, from the site detection map 50, in correspondence with the observation that the crux cordis 36 and the pulmonary artery 37 are missing, it is also possible to recognize, in the corresponding ultrasound examination images, that those sites are missing.

Figure 19:
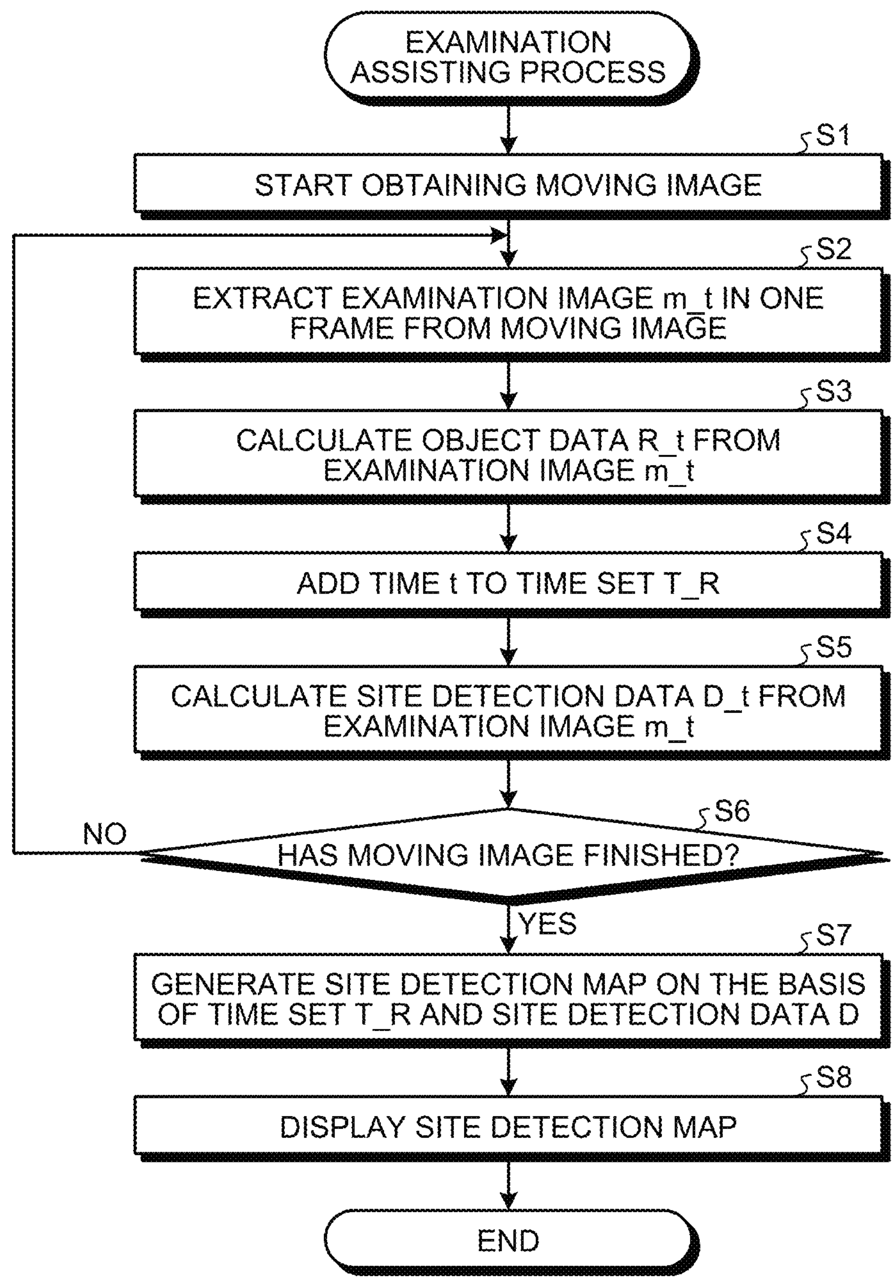
FIG. 19 is a flowchart illustrating an example of an examination assisting process according to the first embodiment.

Next, an operation of the examination assisting apparatus 100 according to the first embodiment will be explained. FIG. 19 is a flowchart illustrating an example of an examination assisting process according to the first embodiment.

When being instructed to start obtaining a moving image, the obtaining unit 131 starts obtaining a moving image on the basis of the reception data obtained from the probe 110 (step S1). The obtaining unit 131 stores the obtained moving image into the image storage unit 121 and also outputs the obtained moving image to the judging unit 132.

When having received the input of the moving image from the obtaining unit 131, the judging unit 132 extracts an examination image $m_t$ in one frame from the input moving image (step S2). The judging unit 132 calculates object data $R_t$ from the extracted examination image $m_t$ (step S3). When having determined that the examination image $m_t$ renders the structure H (the heart) of the object serving as the examined subject, the judging unit 132 adds the time t to the time set $T_R$ (step S4). The judging unit 132 stores the calculated object data $R_t$ and the time set $T_R$ into the object data storage unit 122. Further, the judging unit 132 outputs the extracted examination image $m_t$ to the detecting unit 133.

When having received the input of the examination image $m_t$ from the judging unit 132, the detecting unit 133 refers to the learning model storage unit 123 and performs the process of detecting the elements h (the sites) of the structure H (the heart) of the object on the input examination image $m_t$, by using the learning model. In other words, the detecting unit 133 calculates site detection data $D_t$ from the examination image $m_t$ (step S5) The detecting unit 133 stores the calculated site detection data $D_t$ into the site detection data storage unit 124 and also outputs an end judging instruction to the judging unit 132.

When having received the input of the end judging instruction from the detecting unit 133, the judging unit 132 judges whether or not the moving image has finished (step S6). When having determined that the moving image has not finished (step S6: No), the judging unit 132 advances the time t by 1, i.e., advances the moving image by one frame, and returns to step S2. On the contrary, when having determined that the moving image has finished (step S6: Yes), the judging unit 132 outputs a generation instruction to the display controlling unit 134.

When having received the input of the generation instruction from the judging unit 132, the display controlling unit 134 refers to the object data storage unit 122 and obtains the time set $T_R$. Further, the display controlling unit 134 refers to the site detection data storage unit 124 and obtains the site detection data D corresponding to the time set $T_R$. On the basis of the time set $T_R$ and the site detection data D, the display controlling unit 134 generates a site detection map (step S7). The display controlling unit 134 outputs the generated site detection map to the display unit 111 and causes the display unit 111 to display the site detection map (step S8). As a result, the examination assisting apparatus 100 is able to provide the site detection map that makes it possible to easily judge whether an abnormality is present or absent. Further, even when the level of precision of the scan is not sufficient or when the examined subject significantly changes in the course of time, the examination assisting apparatus 100 is able to provide information useful for diagnosing processes by displaying the detection results of the sites (the results of the object recognition) chronologically. Further, because using the site detection map enables the viewer to see, in a list view, the manner in which the sites are detected in the entire moving image of the examined subject, the examination assisting apparatus 100 is able to reduce the time involved in the viewer's checking process. Further, because the examination assisting apparatus 100 makes it possible to identify the sites regardless of the skills of users (examiners), it is possible to keep variations in examination results small among the users.

When the present embodiment is compared with related ultrasound examinations, during a related ultrasound examination, an examination may be performed depending on whether a specific site is properly rendered in an image of a two-dimensionally scanned cross-sectional plane. The quality of the image of the two-dimensionally scanned cross-sectional plane from the examination is not stable due to noise, shadows, movements of the examined subject, and the like. It would therefore be difficult to directly detect the sites. In contrast, the examination assisting apparatus 100 according to the present embodiment performs the site detecting process that uses the object detection technique on each of the plurality of ultrasound examination images and displays the site detection map in which the detection result of each of the plurality of sites included in the examined subject is kept in correspondence with the scan. As a result, the examiner is able to easily perform the examination by referring to the site detection map.

Next, an ultrasound examination using the examination assisting apparatus 100 according to the present embodiment will be compared with a related ultrasound examination. For example, during the related ultrasound examination, an examination may be performed by checking for a plurality of sites in an image of a two-dimensionally scanned cross-sectional plane obtained by using an ultrasound wave. As for the image of the two-dimensionally scanned cross-sectional plane obtained by the ultrasound examination, what is rendered in the image and the quality of the image are not stable due to a plurality of factors including noise, a shadow of a human arm or the like, movements of the examined subject such as pulsation of the heart, and the like. In other words, from among the plurality of images taken on the two-dimensionally scanned cross-sectional planes, the examiner has to check each of a plurality of sites from one or more of the images in which the plurality of sites are recognizable. For this reason, the related ultrasound examination involves skillful and experienced work to identify appropriate images from which each of the plurality of sites is to be checked and to check the statuses of the sites in the identified images. Accordingly, obtaining an appropriate examination result is dependent on the skills of the examiner.

In contrast, the examination assisting apparatus 100 according to the present embodiment performs the site detecting process that uses the object detection technique on each of the plurality of ultrasound examination images and displays the site detection map in which the detection result of each of the plurality of sites included in the examined subject is kept in correspondence with the scan. By performing an ultrasound examination while using this function, the examiner who refers to the site detection map does not have to identify the images in which the plurality of sites are recognizable. For this reason, even examiners who are not experienced and skillful are able to perform examinations with stable quality. Further, when a third person checks examination data in a retrospective manner, even when the examination data is a moving image of two-dimensionally scanned cross-sectional planes obtained from an ultrasound examination, he/she who refers to the site detection map is able to check the examination without having to play back or check the moving image.

In this manner, on each of the plurality of ultrasound examination images taken of the examined subject by performing the scan thereon, the examination assisting apparatus 100 performs the site detecting process that uses the object detection technique. Further, on the basis of the detection results, the examination assisting apparatus 100 displays the site detection map in which the detection result of each of the plurality of sites included in the examined subject is kept in correspondence with the scan. As a result, the examination assisting apparatus 100 is able to provide the site detection map that makes it possible to easily judge whether an abnormality is present or absent.

Further, among one or more of the sites of which the detection result is indicated as undetected and one or more of the sites of which the detection result exhibits a probability lower than a predetermined value, when at least one of such sites is consecutively observed in the scan for a time period equal to or longer than the predetermined length of time, the examination assisting apparatus 100 displays, in a highlighted manner, the part of the site detection map corresponding to the site. As a result, the examination assisting apparatus 100 is able to advise about the site having a high possibility of being abnormal.

Further, with respect to a detection result in which all of the plurality of sites are indicated as undetected, the examination assisting apparatus 100 displays, in a highlighted manner, the part of the site detection map corresponding to the detection result. As a result, the examination assisting apparatus 100 is able to advise about the detection result (the examination image) having a high possibility of the scan being defective.

Further, the examination assisting apparatus 100 displays the detection results in the different modes in accordance with the indication as being undetected and the probabilities of the detection results. As a result, the examination assisting apparatus 100 is able to provide the site detection map having a high degree of at-a-glance convenience.

Further, when any one of the detection results is designated in the site detection map, the examination assisting apparatus 100 displays the ultrasound examination image corresponding to the designated detection result. As a result, the examination assisting apparatus 100 is able to display the ultrasound examination image corresponding to the detection result having a high possibility of being abnormal in the site detection map.

Further, when detection results in which all of the plurality of sites are indicated as undetected are consecutively observed, the examination assisting apparatus 100 displays the information indicating that the scan is defective. As a result, the examination assisting apparatus 100 is able to prompt the user to perform a re-examination.

Further, the scan performed by the examination assisting apparatus 100 is a scan in a forward direction. As a result, the examination assisting apparatus 100 is able to display the site detection map corresponding to the scan performed in the forward direction.

Further, the scan performed by the examination assisting apparatus 100 is one selected from among: a slide scan, a rotation scan, a fan-shaped scan, a pendulum scan, and a scan combining any of these scans. As a result, the examination assisting apparatus 100 is able to display the site detection map corresponding to the scanning method being used.

Next, a related technique used for presenting information about an arbitrary cross-sectional plane based on a scan result obtained by implementing CT, MRI, or the like will be compared with the technique of the present embodiment used for generating and displaying the site detection map.

When the information about the cross-sectional plane is presented on the basis of the scan result obtained by implementing CT, MRI, or the like, generating a three-dimensional model involves measured data having a sufficient level of precision. Further, such a technique expects that the measured data does not significantly vary in the course of time. However, it is difficult to obtain such measured data that has a sufficient level of precision from ultrasound examinations. It would therefore be difficult to structure a three-dimensional model to present the information about the cross-sectional plane by using the related technique.

In contrast, the examination assisting apparatus 100 according to the present embodiment is able to perform the site detecting process that uses the object detection technique on each of the plurality of ultrasound examination images and to display the site detection map in which the detection result of each of the plurality of sites included in the examined subject is kept in correspondence with the scan.

[b] Second Embodiment

In the first embodiment above, the example using the fetal heart as the examined subject is explained. However, the present disclosure is applicable to any object as long as it is possible to perform an ultrasound examination thereon. For example, the examined subject may be a semiconductor package. An embodiment in this situation will be explained as a second embodiment. In the second embodiment, only the examined subject is different from that of the examination assisting apparatus 100 according to the first embodiment. Thus, the examined subject will be explained in the following sections, and duplicate explanations of configurations and operations will be omitted.

In recent years, in more and more semiconductor packages, a large number of chips and the like (components) are installed in a single package called a System in Package (SiP), owing to the advancement of three-dimensional mounting technology. Because such semiconductor packages have a complicated internal structure, there is a demand not only for the capability of detecting flaws by performing a related ultrasound examination, but also for the capability of checking the installation status of the internal structure.

Figure 20:
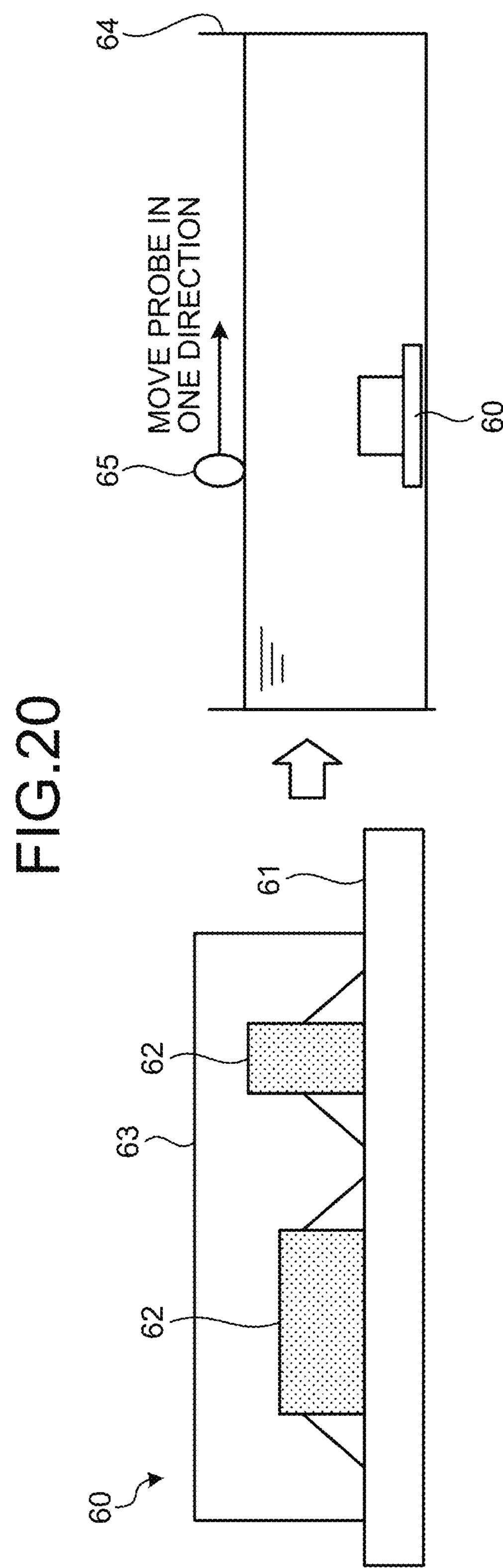
FIG. 20 is a drawing illustrating examples of an examined subject and an examination method according to a second embodiment.

FIG. 20 is a drawing illustrating examples of an examined subject and an examination method according to the second embodiment. A package 60 illustrated in FIG. 20 is an example of a semiconductor package. In the package 60, a plurality of chips 62 are mounted on a substrate 61 and are sealed by package resin 63. In the second embodiment, the package 60 is placed at the bottom of a water tank 64, so as to obtain an examination image by moving a probe 65 parallel to the surface of the water in the water tank 64. The probe 65 corresponds to the probe 110 of the examination assisting apparatus 100.

In the second embodiment, the examination assisting apparatus 100 calculates object data R_t on the basis of a design drawing of the package 60. In other words, in the second embodiment, on the basis of the design drawing of the package 60, the examination assisting apparatus 100 calculates the object data R_t by obtaining the types of components that are supposed to be rendered in the examination image m_t representing a cross-sectional plane and the time t. Further, in correspondence with the time periods in which the components are supposed to be rendered, the examination assisting apparatus 100 calculates a time set T_R. In this situation, because the calculation of the object data R_t is performed in the same manner as in the first embodiment, the explanation thereof will be omitted.

Figures 21, 22:
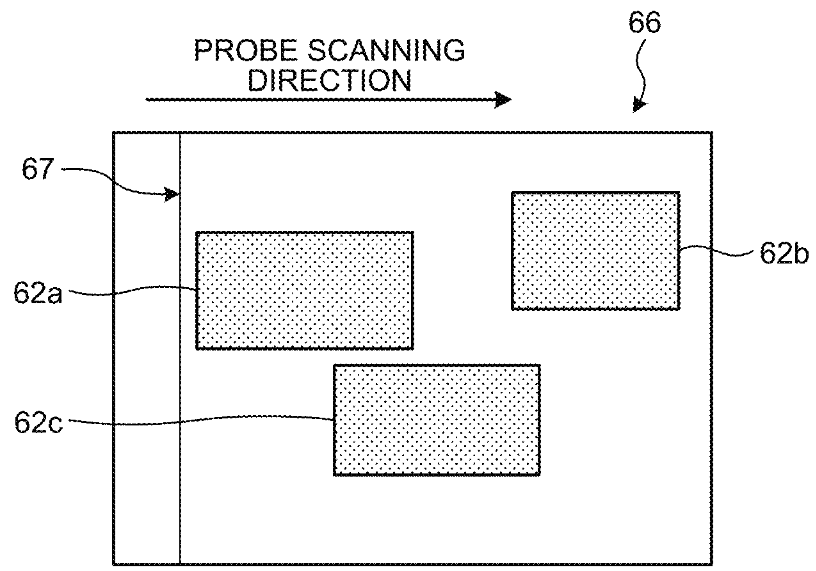
FIG. 21 is a drawing illustrating examples of components that are supposed to be rendered.
FIG. 22 is a drawing illustrating an example of a site detection map according to the second embodiment.

FIG. 21 is a drawing illustrating examples of the components that are supposed to be rendered. As illustrated in FIG. 21, a plan view 66 of the package 60 indicates a plurality of chips 62*a*, 62*b*, and 62*c* as the components that are supposed to be rendered. In the second embodiment, when a cross-sectional plane 67 is moved in a probe scanning direction, a site detection map, i.e., a probability map D(h,t) is generated with respect to the chips 62*a*, 62*b*, and 62*c*. In the second embodiment, the time set T_R is made up of times t corresponding to the time period from the point at which the chip 62*a* appears on the cross-sectional plane 67 to the point at which the chip 62*b* disappears from the cross-sectional plane 67.

The examination assisting apparatus 100 calculates site detection data D_t from the examination images m_t. On the basis of the time set T_R and the site detection data D corresponding to the time set T_R, the examination assisting apparatus 100 generates the site detection map, i.e., the probability map D(h,t). The display controlling unit 134 outputs the generated site detection map to the display unit 111 and causes the display unit 111 to display the site detection map. Because the calculation of the site detection data D_t is performed in the same manner as in the first embodiment, the explanation thereof will be omitted.

FIG. 22 is a drawing illustrating an example of the site detection map according to the second embodiment. A site detection map 68 illustrated in FIG. 22 is an example of the site detection map corresponding to the plan view 66 of the package 60. The site detection map 68 illustrated in FIG. 22 indicates values of the probability map D(h,t) while the vertical axis expresses the chips serving as the elements h, whereas the horizontal axis expresses the cross-sectional planes (the examination images) corresponding to the times t. As illustrated in FIG. 22, the site detection map 68 displays the probability of each of the cross-sectional planes with respect to each of the chips 62*a*, 62*b*, and 62*c*. In this situation, for example, when the package resin 63 has an air bubble, although it is not possible to see a chip 62 positioned underneath the air bubble by simply looking at the examination image of the cross-sectional plane, it is possible to learn that the chip 62 is present by looking at the probabilities of the cross-sectional planes. Further, from the site detection map 68, it is possible to recognize, at a glance, the installation state including a relationship among the positions of the chips 62*a*, 62*b*, and 62*c*. As explained herein, even when the examined subject is the semiconductor package, the examination assisting apparatus 100 according to the second embodiment is capable of providing the site detection map on the basis of the results from the ultrasound examination images.

In the embodiments described above, the scanning direction is indicated in FIGS. 13, 16, 20, and 21; however, possible scanning directions are not limited to those illustrated in the drawings. For instance, it is also acceptable to identify the scanning direction by comparing the frames in the moving image with one another, to calculate the object data R_t and the site detection data D_t from a set made up of examination images in a predetermined span excluding duplicate frames, and to generate a site detection map of the predetermined span.

In the embodiments described above, YOLO, SSD, and Faster-RNN are mentioned as examples of the object detection algorithms; however, possible examples are not limited to these. For instance, it is acceptable to use an object detection algorithm using any of various types of neural networks such as DPM, Fast-RNN, or the like. Further, as the learning method, it is possible to use any of various publicly-known methods other than backpropagation methods. Further, neural networks have, for example, a multilayer structure including an input layer, an intermediate layer (a hidden layer), and an output layer, while the layers have such a structure in which a plurality of nodes are connected by edges. Each of the layers has a mathematical function called an "activation function". Each of the edges has a "weight". The value of each of the nodes is calculated from the values of the nodes in a previous layer, the values of the weights of the connecting edges, and the activation function of the layer. As for the calculation method, it is possible to use any of various publicly-known methods. As for the machine learning, besides the neural network scheme, it is possible to use any of various methods such as a Support Vector Machine (SVM) method.

The constituent elements of the functional units illustrated in the drawings do not necessarily have to be physically configured as indicated in the drawings. In other words, specific modes of distribution and integration of the functional units are not limited to those illustrated in the drawings. It is acceptable to functionally or physically distribute or integrate all or a part of the functional units in any arbitrary units, depending on various loads, the status of use, and the like. For example, the judging unit 132 and the detecting unit 133 may be integrated together. Further, the processes illustrated in the drawings do not have to be performed in the order described above. As long as no conflict occurs in the processing, it is acceptable to perform certain processes simultaneously and to change the order in which certain processes are performed.

Further, as for the various types of processing functions implemented by the apparatuses and the devices, all or an arbitrary part thereof may be executed by a Central Processing Unit (CPU) (or a microcomputer such as a Micro Processing Unit (MPU), a Micro Controller Unit (MCU), or the like). Further, needless to say, it is acceptable to execute all or an arbitrary part of the various types of processing functions by using a program analyzed and executed by a CPU (or a microcomputer such as an MPU, an MCU, or the like) or by using hardware structured with wired logic.

Figure 23:
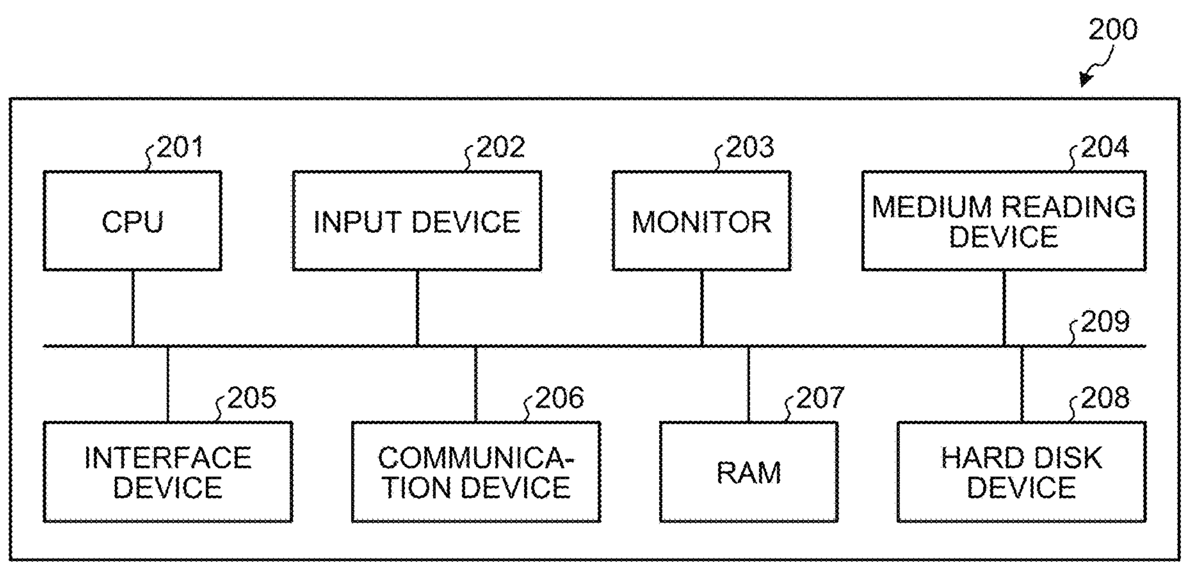
FIG. 23 is a drawing illustrating an example of a computer that executes an examination assisting program.

Further, it is possible to realize the various types of processes explained in the above embodiments by causing a computer to execute a program prepared in advance. Thus, in the following sections, an example of the computer that executes a program having the same functions as those described in the above embodiments will be explained. FIG. 23 is a drawing illustrating an example of a computer that executes an examination assisting program.

As illustrated in FIG. 23, a computer 200 includes a CPU 201 that executes various type of computing processes, an input device 202 that receives data inputs, and a monitor 203. Further, the computer 200 includes a medium reading device 204 that reads a program and the like from a storage medium, an interface device 205 used for connecting to various types of devices, and a communication device 206 used for connecting in a wired or wireless manner to other information processing apparatuses or the like. Further, the computer 200 includes a RAM 207 that temporarily stores therein various types of information and a hard disk device 208. Further, the devices 201 to 208 are connected to a bus 209.

The hard disk device 208 stores therein the examination assisting program having the same functions as those of processing units illustrated in FIG. 1 such as the obtaining unit 131, the judging unit 132, the detecting unit 133, and the display controlling unit 134. Further, the hard disk device 208 stores therein various types of data for realizing the image storage unit 121, the object data storage unit 122, the learning model storage unit 123, the site detection data storage unit 124, and the examination assisting program. For example, the input device 202 receives inputs of various types of information such as operation information, from a user of the computer 200. For example, the monitor 203 displays various types of screens such as display screens, for the user of the computer 200. For example, the interface device 205 has a probe or the like connected thereto. For example, the communication device 206 is connected to a network (not illustrated) and exchanges various types of information with the other information processing apparatuses.

The CPU 201 performs various types of processes by reading programs stored in the hard disk device 208, loading the read programs into the RAM 207, and executing the programs. Further, these programs are able to cause the computer 200 to function as the obtaining unit 131, the judging unit 132, the detecting unit 133, and the display controlling unit 134 illustrated in FIG. 1.

The examination assisting program described above does not necessarily have to be stored in the hard disk device 208. For example, it is also acceptable to configure the computer 200 to read and execute a program stored in a storage medium that is readable by the computer 200. Examples of the storage medium that is readable by the computer 200 include portable recording media such as a Compact Disk Read-Only Memory (CD-ROM), a Digital Versatile Disc (DVD), and a Universal Serial Bus (USB) memory; semiconductor memory elements such as a flash memory; a hard disk drive, and the like. Further, it is also acceptable to store the examination assisting program in apparatuses connected to a public communication line, the Internet, a Local Area Network (LAN), and the like so that the computer 200 reads and executes the examination assisting program from any of these apparatuses.

It is possible to provide the site detection map that makes it possible to easily judge whether an abnormality is present or absent.

All examples and conditional language recited herein are intended for pedagogical purposes of aiding the reader in understanding the invention and the concepts contributed by the inventors to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A non-transitory computer-readable recording medium storing therein an examination assisting program that causes a computer to execute a process comprising:

detecting a site in an examined subject, using an object detection technique, wherein a plurality of sites are included in a structure of the examined subject and the examined subject is determined to be included in each of a plurality of ultrasound examination images taken by performing a scan on the examined subject, the detected site being represented by a probability of a position of the site in the examined subject; and displaying a site detection map that includes a first axis thereof that indicates each of the sites, a second axis thereof that indicates each of the ultrasound examination images and the probability of each of the sites for each of the ultrasound examination images, wherein, displaying includes highlighting a first site included in the sites on the site detection map on condition that the probability of the first site is lower than a predetermined value for first ultrasound examination images that are included in the plurality of ultrasound examination images and are consecutive over a time period equal to or longer than a predetermined length of time.

2. The non-transitory computer-readable recording medium according to claim 1, wherein, displaying includes highlighting an ultrasound examination image among the ultrasound examination images indicated on the site detection map wherein the probability of each of the sites for the ultrasound examination image is indicated as undetected.

3. The non-transitory computer-readable recording medium according to claim 1, wherein on the site detection map, the sites for each of the ultrasound examination images are displayed in different display formats in accordance with respective probabilities of the sites.

4. The non-transitory computer-readable recording medium according to claim 1, wherein, when a site among the sites for an ultrasound examination image among the ultrasound examination images is designated on the site detection map, the displaying includes displaying the ultrasound examination image.

5. The non-transitory computer-readable recording medium according to claim 1, wherein, when the probability of each of the sites for ultrasound examination images that are highlighted included in the plurality of ultrasound examination images and are consecutive on the site detection map is indicated as undetected, the displaying includes displaying information indicating that the scan is defective.

6. The non-transitory computer-readable recording medium according to claim 1, wherein the scan is a scan performed in a one direction over the examined subject.

7. The non-transitory computer-readable recording medium according to claim 1, wherein the scan is one selected from among: a slide scan, a rotation scan, a fan-shaped scan, a pendulum scan, and a combination of any of these scans.

8. An examination assisting method implemented by a computer to perform processes of:

detecting a site in an examined subject, using an object detection technique, wherein a plurality of sites are included in a structure of the examined subject and the examined subject is determined to be included in each of a plurality of ultrasound examination images taken by performing a scan on the examined subject, the detected site being represented by a probability of a position of the site in the examined subject, by a processor; and displaying a site detection map that includes a first axis thereof that indicates each of the sites, a second axis thereof that indicates each of the ultrasound examination images and the probability of each of the sites for each of the ultrasound examination images, wherein, displaying includes highlighting a first site included in the sites on the site detection map on condition that the probability of the first site is lower than a predetermined value for first ultrasound examination images that are included in the plurality of ultrasound examination images and are consecutive over a time period equal to or longer than a predetermined length of time.

9. The examination assisting method according to claim 8, further comprising indicating that the scan is defective on condition that the probability of each of the sites for ultrasound examination images are highlighted.

10. The examination assisting method according to claim 8, further comprising, on the site detection map, displaying sites for an ultrasound examination image in different display formats in accordance with respective probabilities of each site.

11. An examination assisting apparatus comprising:

a processor configured to:

detect a site in an examined subject, using an object detection technique, wherein a plurality of sites are included in a structure of the examined subject and the examined subject is determined to be included in each of a plurality of ultrasound examination images taken by performing a scan on the examined subject, the detected site being represented by a probability of a position of the site in the examined subject; and display a site detection map that includes a first axis thereof that indicates each of the sites, a second axis thereof that indicates each of the ultrasound examination images and the probability of each of the sites for each of the ultrasound examination images, including highlighting a first site included in the sites on the site detection map on condition that the probability of the first site is lower than a predetermined value for first ultrasound examination images that are included in the plurality of ultrasound examination images and are consecutive over a time period equal to or longer than a predetermined length of time.

12. The examination assisting apparatus according to claim 11, wherein, when the processor is configured to indicate that the scan is defective on condition that the probability of each of the sites for the ultrasound examination images are highlighted.

13. The examination assisting apparatus according to claim 11, wherein on the site detection map, sites for an ultrasound examination image are displayed in different display formats in accordance with respective probabilities of each site.

* * * * *